US011986260B2

(12) United States Patent
Elbanna et al.

(10) Patent No.: US 11,986,260 B2
(45) Date of Patent: May 21, 2024

(54) ROBOTIC SURGICAL SYSTEM AND METHODS UTILIZING VIRTUAL BOUNDARIES WITH VARIABLE CONSTRAINT PARAMETERS

(71) Applicant: MAKO Surgical Corp., Weston, FL (US)

(72) Inventors: Jamil Elbanna, San Diego, CA (US); Michael Prieto, Miami Springs, FL (US); Vijay Subramanian, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 212 days.

(21) Appl. No.: 17/724,634

(22) Filed: Apr. 20, 2022

(65) Prior Publication Data

US 2022/0241036 A1 Aug. 4, 2022

Related U.S. Application Data

(63) Continuation of application No. 16/816,782, filed on Mar. 12, 2020, now Pat. No. 11,337,766.
(Continued)

(51) Int. Cl.
  *A61B 17/16* (2006.01)
  *A61B 17/17* (2006.01)
  (Continued)

(52) U.S. Cl.
  CPC .......... *A61B 34/30* (2016.02); *A61B 17/1615* (2013.01); *A61B 17/1626* (2013.01);
  (Continued)

(58) Field of Classification Search
  None
  See application file for complete search history.

(56) References Cited

U.S. PATENT DOCUMENTS 5,299,288 A * 3/1994 Glassman .............. B25J 9/1679
  623/908
7,035,716 B2 4/2006 Harris et al.
(Continued)

FOREIGN PATENT DOCUMENTS

CN 104287836 A 1/2015
CN 106725711 A 5/2017
(Continued)

OTHER PUBLICATIONS

English language abstract and machine-assisted English translation for CN 104287836 extracted from espacenet.com database on Apr. 29, 2020, 5 pages.
(Continued)

*Primary Examiner* — Christian A Sevilla
(74) *Attorney, Agent, or Firm* — Howard & Howard Attorneys PLLC

(57) ABSTRACT

Surgical systems and methods for utilizing virtual boundaries having different constraint parameters. A robotic manipulator supports and moves a surgical tool for treating a bone structure. A navigation system tracks the surgical tool and the bone structure. Controller(s) obtain a virtual model of the bone structure and define first and second virtual boundaries relative to the virtual model. The first virtual boundary has a first constraint parameter and the second virtual boundary has a second constraint parameter that is different than the first constraint parameter. The virtual model and virtual boundaries are registered to the bone structure. The manipulator moves the surgical tool relative to the bone structure and the first and second virtual boundaries. The surgical tool is constrained relative to the first virtual boundary in accordance with the first constraint parameter and constrained relative to the second virtual boundary in accordance with the second constraint parameter.

20 Claims, 15 Drawing Sheets

Related U.S. Application Data

(60) Provisional application No. 62/819,077, filed on Mar. 15, 2019.

(51) Int. Cl.
*A61B 34/00* (2016.01)
*A61B 34/30* (2016.01)
*A61B 34/10* (2016.01)
*A61B 34/20* (2016.01)
*A61B 90/00* (2016.01)

(52) U.S. Cl.
CPC .......... *A61B 17/1757* (2013.01); *A61B 34/25* (2016.02); *A61B 2034/107* (2016.02); *A61B 2034/2055* (2016.02); *A61B 2034/306* (2016.02); *A61B 2090/062* (2016.02); *A61B 2090/066* (2016.02)

(56) References Cited

U.S. PATENT DOCUMENTS

| | | | |
|---|---|---|---|
| 7,747,311 B2 | 6/2010 | Quaid, III | |
| 8,010,180 B2 | 8/2011 | Quaid et al. | |
| 8,615,286 B2 * | 12/2013 | Shen | A61B 34/20 600/424 |
| 8,894,654 B2 | 11/2014 | Anderson | |
| 9,008,757 B2 | 4/2015 | Wu | |
| 9,119,655 B2 | 9/2015 | Bowling et al. | |
| 9,131,597 B2 | 9/2015 | Taft et al. | |
| 9,179,875 B2 | 11/2015 | Hua | |
| 9,314,239 B2 | 4/2016 | Brown | |
| 9,554,838 B2 | 1/2017 | Sharkey et al. | |
| 9,603,665 B2 | 3/2017 | Bowling et al. | |
| 9,649,164 B2 | 5/2017 | Kim et al. | |
| 9,848,834 B2 | 12/2017 | Park et al. | |
| 10,004,565 B2 | 6/2018 | Kang et al. | |
| 10,098,704 B2 | 10/2018 | Bowling et al. | |
| 10,130,477 B2 | 11/2018 | Donner et al. | |
| 10,245,087 B2 | 4/2019 | Donner et al. | |
| 10,314,661 B2 | 6/2019 | Bowling et al. | |
| 10,433,880 B2 | 10/2019 | Donner et al. | |
| 10,492,802 B2 | 12/2019 | Donner et al. | |
| 10,548,619 B2 | 2/2020 | Wallace et al. | |
| 10,588,645 B1 | 3/2020 | Cao et al. | |
| 10,888,337 B2 | 1/2021 | Shen et al. | |
| 11,253,329 B2 | 2/2022 | Bowling | |
| 2005/0177169 A1 | 8/2005 | Fisher et al. | |
| 2007/0142751 A1 | 6/2007 | Kang et al. | |
| 2011/0190774 A1 | 8/2011 | Nikolchev et al. | |
| 2011/0245833 A1 | 10/2011 | Anderson | |
| 2012/0179070 A1 | 7/2012 | Pommer et al. | |
| 2014/0039454 A1 | 2/2014 | Sharkey | |
| 2014/0039517 A1 * | 2/2014 | Bowling | A61B 34/74 606/130 |
| 2014/0208578 A1 | 7/2014 | Linderman et al. | |
| 2014/0222023 A1 * | 8/2014 | Kim | A61B 34/30 606/130 |
| 2014/0276949 A1 * | 9/2014 | Staunton | A61B 34/30 606/130 |
| 2015/0150616 A1 | 6/2015 | Sharkey et al. | |
| 2015/0209056 A1 | 7/2015 | Shoham et al. | |
| 2016/0331467 A1 | 11/2016 | Slamin et al. | |
| 2016/0354162 A1 | 12/2016 | Yen et al. | |
| 2017/0065347 A1 | 3/2017 | Bojarski et al. | |
| 2017/0079727 A1 | 3/2017 | Crawford et al. | |
| 2017/0312039 A1 | 11/2017 | Crawford et al. | |
| 2017/0325845 A1 | 11/2017 | Donner et al. | |
| 2018/0014890 A1 | 1/2018 | Stanton et al. | |
| 2018/0014891 A1 | 1/2018 | Krebs et al. | |
| 2018/0035893 A1 | 2/2018 | Donner et al. | |
| 2018/0042684 A1 | 2/2018 | Kostrzewski et al. | |
| 2018/0078201 A1 | 3/2018 | Behzadi | |
| 2018/0092669 A1 | 4/2018 | Donner et al. | |
| 2018/0110573 A1 | 4/2018 | Kostrzewski | |
| 2018/0168750 A1 | 6/2018 | Staunton et al. | |
| 2018/0199951 A1 | 7/2018 | Chappuis et al. | |
| 2018/0271602 A1 | 9/2018 | Frey et al. | |
| 2018/0289432 A1 | 10/2018 | Kostrzewski et al. | |
| 2018/0318019 A1 | 11/2018 | Bos | |
| 2018/0325608 A1 | 11/2018 | Kang et al. | |
| 2019/0069882 A1 | 3/2019 | Moctezuma de la Barrera et al. | |
| 2019/0090966 A1 | 3/2019 | Kang et al. | |
| 2019/0133663 A1 | 5/2019 | Sharkey et al. | |
| 2019/0209011 A1 | 7/2019 | Donner et al. | |
| 2019/0247057 A1 | 8/2019 | Anderson | |
| 2019/0262078 A1 | 8/2019 | Lang | |
| 2019/0314040 A1 | 10/2019 | Greenhalgh et al. | |
| 2019/0314158 A1 | 10/2019 | Sharkey et al. | |
| 2019/0336220 A1 | 11/2019 | Hladio et al. | |
| 2019/0343640 A1 | 11/2019 | Donner et al. | |
| 2020/0015909 A1 | 1/2020 | Stawiaski et al. | |
| 2020/0029979 A1 | 1/2020 | Donner et al. | |
| 2020/0030046 A1 | 1/2020 | Bowling et al. | |
| 2020/0054215 A1 | 2/2020 | Roche | |
| 2020/0093611 A1 | 3/2020 | Forstein et al. | |
| 2020/0121404 A1 | 4/2020 | Morard et al. | |
| 2020/0289133 A1 | 9/2020 | Elbanna et al. | |
| 2020/0324408 A1 | 10/2020 | Bourlion et al. | |

FOREIGN PATENT DOCUMENTS

| | | | |
|---|---|---|---|
| WO | 2009092164 A1 | 7/2009 | |
| WO | WO-2009092164 A1 * | 7/2009 | ............. A61B 34/20 |
| WO | 2017137087 A1 | 8/2017 | |

OTHER PUBLICATIONS

English language abstract and machine-assisted English translation for CN 106725711 extracted from espacenet.com database on Apr. 29, 2020, 8 pages.

Hu, Ying et al., "State Recognition of Pedicle Drilling With Force Sensing in a Robotic Spinal Surgical System", EEEE/ASME Transactions on Mechatronics, vol. 19, No. 1, Feb. 2014, http://ieeexplore.ieee.org/abstract/document/6422395, pp. 357-365.

International Search Report for Application No. PCT/US2020/022352 dated Jul. 3, 2020, 4 pages.

Ortmaier, H. et al., "Experiments on Robot-Assisted Navigated Drilling and Milling of Bones For Pedicle Screw Placement", Int J Med Robotics Comput Assist Surg, vol. 2, Dec. 2006, https://doi.org/10.1002/rcs, pp. 350-363.

Rampersaud, Raja et al., "Accuracy Requirements for Image-Guided Spinal Pedicle Screw Placement", SPINE, vol. 26, No. 4, 2001, pp. 352-359.

Zevallos, Nicolas et al., "A Surgical System for Automatic Registration, Stiffness Mapping and Dynamic Image Overlay," 2018 International Symposium on Medical Robotics (ISMR), doi: 10.1109/ISMR.2018.8333310, 2018, pp. 1-6.

* cited by examiner

ROBOTIC SURGICAL SYSTEM AND METHODS UTILIZING VIRTUAL BOUNDARIES WITH VARIABLE CONSTRAINT PARAMETERS

CROSS-REFERENCE TO RELATED APPLICATIONS

The subject application is a continuation of U.S. patent application Ser. No. 16/816,782, filed Mar. 12, 2020, which claims priority to and all the benefits of U.S. Provisional Patent App. No. 62/819,077, filed Mar. 15, 2019, the contents of each of the aforementioned applications being are hereby incorporated by reference in their entirety.

BACKGROUND

Robotic systems for performing surgical procedures in a patient's spine are known. For instance, robotic systems are currently utilized to place pedicle screws in a patient's spine. Robotics have also been used to provide a "drill guide" or "bushing" that is aligned with the spine pedicle trajectory. Such drill guides are used by the surgeon to drill a pilot hole in the pedicle and then place a guide pin in the pedicle. Pedicle screws are then passed over said guide pin. Several challenges to achieving the required accuracy are typically experienced in this process due to skiving at the entry point of the pedicle, inaccuracies in the registration/mapping of the spine CT scanned model with the robot's coordinate system, and movement of the vertebral bodies due to patient positioning and/or intraoperatively due to screw placement and/or decompression and/or disc height restoration. Furthermore, pedicle cannulation is susceptible to error, such as breaching of a pedicle wall. In turn, such errors can lead to potential nerve injury inflicted by the tool used for cannulation or the pedicle screw, when inserted.

SUMMARY

A first aspect of the disclosure involves a surgical system configured for manipulation of a bone structure comprising a first cortical region, a second cortical region and a cancellous bone region between the first and second cortical regions, the surgical system comprising: a surgical tool comprising a cutting bur rotatable about a cutting axis; a robotic manipulator comprising a plurality of links and joints and being configured to support and move the surgical tool; and one or more controllers being configured to control movement of one or more of the joints of the robotic manipulator and to control operation of the surgical tool to: align the cutting axis to a target axis associated with the bone structure; advance the cutting bur along the target axis and to rotate the cutting bur about the cutting axis to penetrate the first cortical region of the bone structure to create an entry point; and advance the cutting bur through the entry point and into the cancellous bone region to displace and cannulate the cancellous bone region with the cutting bur.

In some implementations, to advance the cutting bur through the cancellous bone region, the one or more controllers are configured to control operation of the surgical tool to rotate the cutting bur about the cutting axis to displace and cannulate the cancellous bone region.

In some implementations, one or more sensors are configured to sense forces applied to the cutting bur by the cancellous bone region, wherein, to advance the cutting bur through the cancellous bone region, the one or more controllers are configured to: compare the sensed forces to a predetermined force threshold defined to prevent displacement of the bone structure from force applied by the cutting bur; and adjust one or more of a rotational cutting speed of the cutting bur and a feed rate of the surgical tool to maintain advancement of the cutting bur through the cancellous bone region and to maintain the sensed forces relative to the force threshold. In some implementations, the force is specifically axial force applied along the cutting axis. In some implementations, the force is specifically lateral force applied transverse to the cutting axis. In some implementations, the force is a combination of lateral and axial force.

In some implementations, to advance the cutting bur through the cancellous bone region, the one or more controllers are configured to control operation of the surgical tool to disable rotation of the cutting bur about the cutting axis.

In some implementations, one or more sensors are configured to sense forces applied to the cutting bur, and based on the sensed forces, the one or more controllers are configured to adjust control of one or more of movement of the robotic manipulator and operation of the surgical tool.

In some implementations, based on the sensed forces, the one or more controllers are configured to detect a transition between the first cortical region and the cancellous bone region or between the cancellous bone region and the second cortical region, and in response to detection of the transition, the one or more controllers are configured to adjust control of one or more of movement of the robotic manipulator and operation of the surgical tool.

In some implementations, one or more sensors are defined as one or more of the following: one or more force/torque transducers configured to sense forces/torques applied to the cutting bur by the bone structure in six-degrees of freedom; one or more sensors coupled to an actuator of the surgical tool and being configured to sense current draw of the actuator responsive to torque applied to the cutting bur by the bone structure; one or more pressure sensors coupled to the surgical tool, cutting bur, or robotic manipulator and being configured to sense pressure applied to the cutting bur by the bone structure; one or more displacement sensors configured to sense displacement of the cutting bur relative to a reference point; and one or more depth sensors configured to sense depth of the cutting bur relative to a reference point.

In some implementations, one or more sensors are configured to sense forces applied to the cutting bur by the first cortical region, and based on the sensed forces, the one or more controllers adjust control of one or more of movement of the robotic manipulator and operation of the surgical tool by being configured to perform one or more of the following: adjust orientation cutting axis to deflect the cutting bur relative to the first cortical region; adjust a rotational cutting speed of the cutting bur; adjust a feed rate of the surgical tool; and retract the cutting bur away from the first cortical region.

In some implementations, one or more sensors are configured to sense forces applied to the cutting bur by the second cortical region, and based on the sensed forces, the one or more controllers adjust control of one or more of movement of the robotic manipulator and operation of the surgical tool by being configured to perform one or more of the following: adjust orientation of the cutting axis to deflect the cutting bur relative to the second cortical region;
  adjust a rotational cutting speed of the cutting bur; adjust a feed rate of the surgical tool; reverse a rotational cutting direction of the cutting bur; and retract the cutting bur away from the second cortical region.

In some implementations, the one or more controllers are configured to: define a first virtual boundary configured to constrain lateral movement of the cutting bur; define a second virtual boundary configured to constrain lateral movement of the cutting bur, wherein the second virtual boundary provides greater lateral compliance for the cutting bur than the first virtual boundary; laterally constrain the cutting bur according to the first virtual boundary to penetrate the first cortical region; and laterally constrain the cutting bur according to the second virtual boundary to advance the cutting bur through the cancellous bone region.

In some implementations, the robotic manipulator comprises a distal link, and a force/torque transducer that is coupled between the surgical tool and the distal link and is configured to sense forces/torques externally applied to the surgical tool in six-degrees of freedom; the one or more controllers are configured to operate the robotic manipulator in a manual mode wherein the one or more controllers are configured to determine a commanded position of the surgical tool based on the forces/torques are applied externally to the surgical tool; and the one or more controllers are configured to control the robotic manipulator in the manual mode to: advance the cutting bur along the target axis and to rotate the cutting bur about the cutting axis to penetrate the first cortical region of the bone structure to create the entry point; and advance the cutting bur through the entry point and into the cancellous bone region to displace and cannulate the cancellous bone region with the cutting bur.

In some implementations, one of the plurality of links of the robotic manipulator is a distal link, and wherein the surgical tool is coupled to the distal link, and comprising a control interface integrated with the surgical tool, coupled to the one or more controllers and comprising tactile controls configured to enable user control of a feed rate of the surgical tool.

In some implementations, one or more sensors configured to sense forces applied to the cutting bur; and wherein the one or more controllers are configured to: control the robotic manipulator to advance the cutting bur along the target axis according to a first feed rate (FR1) to penetrate the first cortical region; based on the sensed forces, detect a transition between the first cortical region and the cancellous bone region; and in response to detecting the transition between the first cortical region and the cancellous bone region, control the robotic manipulator to advance the cutting bur according to a second feed rate; and wherein one of the first feed rate (FR1) and second feed rate is defined and commanded by the one or more controllers based on a surgical plan and wherein the other one of the first feed rate and second feed rate is obtained from user interaction with the tactile controls of the control interface.

In some implementations, one or more controllers are configured to: define a first length of the target axis and a second length of the target axis; control the robotic manipulator to advance the cutting bur along the first length of the target axis according to a first feed rate; and control the robotic manipulator to advance the cutting bur along the second length of the target axis according to a second feed rate; and wherein one of the first feed rate and second feed rate is defined and commanded by the one or more controllers based on a surgical plan and wherein the other one of the first feed rate and second feed rate is obtained from user interaction with the tactile controls of the control interface.

In some implementations, one or more controllers are configured to: detect the cutting bur being located off the target axis and to control the robotic manipulator to advance the cutting bur according to a first feed rate; and detect the cutting bur being located on the target axis and to control the robotic manipulator to advance the cutting bur according to a second feed rate; and wherein one of the first feed rate and second feed rate is defined and commanded by the one or more controllers based on a surgical plan and wherein the other one of the first feed rate and second feed rate is obtained from user interaction with the tactile controls of the control interface.

In some implementations, the first cortical region of the bone structure comprises an actual anatomical landmark, and comprising a navigation system configured to track an actual position of the cutting bur, and wherein: the one or more controllers are configured to control operation of the surgical tool to disable rotation of the cutting bur about the cutting axis and to control the robotic manipulator to cause the cutting bur to interact with the actual anatomical landmarks of the first cortical region; the one or more sensors are configured to sense actual forces applied to the cutting bur by the actual anatomical landmarks of the first cortical region; and the one or more controllers are configured to: store a virtual model of the first cortical region comprising virtual anatomical landmarks of the first cortical region; store data correlating expected force measurements from the one or more sensors and expected positions of the cutting bur to the virtual anatomical landmarks of the first cortical region; receive measurements from the one or more sensors based on actual forces applied to the cutting bur by the actual anatomical landmarks of the first cortical region; receive actual position of the cutting bur from the navigation system; compare the actual force measurements from the one or more sensors and the actual position of the cutting bur from the navigation system with the expected force measurements and the expected positions of the cutting bur to associate the actual anatomical landmarks with one of the virtual anatomical landmarks of the first cortical region; and register the virtual model to the first cortical region based on association of the actual anatomical landmarks with one of the virtual anatomical landmarks of the first cortical region.

In some implementations, the cutting bur comprises a distal tip, a proximal portion, and a peripheral portion disposed between the distal tip and the proximal portion, and wherein the peripheral portion is configured to cut in a direction lateral to the cutting axis to enable the cutting bur to penetrate the first cortical region and wherein a cross-sectional diameter of the distal tip is less than a cross-sectional diameter of the peripheral portion to enable the cutting bur to displace and cannulate the cancellous bone region.

In some implementations, the cutting bur is a spherical bur.

In some implementations, the same cutting bur utilized for cortical region penetration is utilized for cancellous bone cannulation.

In some implementations, a first cutting bur utilized for cortical region penetration and a second cutting bur, different form the first cutting bur is utilized for cancellous bone cannulation.

A second aspect of the disclosure involves a method of operating the surgical system according to the first aspect of the disclosure, and optionally, according to any of the implementations within this section.

A third aspect of the disclosure involves a surgical system for interacting with a bone structure, the surgical system comprising: a robotic manipulator configured to support and move a surgical tool to interact with the bone structure; one or more sensors configured to sense forces applied to the surgical tool by the bone structure; and one or more controllers configured to analyze measurements from the one or more sensors and, in response, control the robotic manipulator and/or the surgical tool.

A fourth aspect of the disclosure involves a method of operating the surgical system according to the third aspect of the disclosure.

The third and fourth aspects of the disclosure are optionally implemented according to any of the implementations within this section.

A fifth aspect of the disclosure involves a surgical system for interacting with a bone structure, the surgical system comprising: a robotic manipulator configured to support and move an end effector relative to the bone structure, the end effector supporting a surgical tool configured to manipulate the bone structure; a control interface integrated with the end effector and being configured to enable manual control of a feed rate of the surgical tool; and one or more controllers configured to control the robotic manipulator to align the surgical tool to a target axis associated with the bone structure and to manage a feed rate of the surgical tool to with respect to the target axis in response to user interaction with the control interface.

In some implementations, one or more sensors configured to sense forces applied to the surgical tool by the bone structure and wherein the one or more controllers are configured to adjust the feed rate in response to the forces applied to the surgical tool.

In some implementations, the bone structure comprises an first cortical region, an second cortical region and a cancellous bone region between the first and second cortical regions, and wherein: the one or more controllers are further configured to control the robotic manipulator to move the surgical tool along the target axis to penetrate the first cortical region and enter the cancellous bone region; the one or more sensors are further configured to sense forces applied to the surgical tool by the first cortical region and/or the cancellous bone region; and the one or more controllers are configured to analyze measurements from the one or more sensors to detect a transition between the first cortical region and the cancellous bone region.

In some implementations, one or more controllers are further configured to control the robotic manipulator to move the surgical tool along the target axis according to a first feed rate to penetrate the first cortical region and enter the cancellous bone region; and in response to detecting the transition between the first cortical region and the cancellous bone region, the one or more controllers are further configured to control the robotic manipulator to move the surgical tool along the target axis according to a second feed rate that is different from the first feed rate to penetrate the cancellous bone region.

In some implementations, the first feed rate to penetrate the first cortical region is less than the second feed rate to penetrate the cancellous bone region.

In some implementations, one or more controllers are further configured to: control the robotic manipulator to move the surgical tool along the target axis according to a first feed rate to penetrate the first cortical region and enter the cancellous bone region, the first feed rate being required by the one or more controllers based on a surgical plan; and in response to detecting the transition between the first cortical region and the cancellous bone region, control the robotic manipulator to move the surgical tool along the target axis according to a second feed rate that is different from the first feed rate to penetrate the cancellous bone region, the second feed rate being manually adjusted by interaction with the control interface integrated with the end effector.

In some implementations, one or more controllers are configured to: define a first length of the target axis and a second length of the target axis; control the robotic manipulator to move the surgical tool along the first length of the target axis according to a first feed rate being required by the one or more controllers based on a surgical plan; and control the robotic manipulator to move the surgical tool along the second length of the target axis according to a second feed rate that is different from the first feed rate, the second feed rate being manually adjusted by interaction with the control interface integrated with the end effector.

In some implementations, one or more controllers are configured to: define a first length of the target axis and a second length of the target axis; control the robotic manipulator to move the surgical tool along the first length of the target axis according to a non-cutting mode wherein the surgical tool is not actuated and passively interacts with the bone structure based on advancement of the surgical tool by the robotic manipulator; control the robotic manipulator to move the surgical tool along the second length of the target axis according to a cutting mode, wherein, in the cutting mode, the surgical tool is actively actuated to remove material from the bone structure.

In some implementations, one or more controllers are configured to: in response to the surgical tool being located off the target axis, control the robotic manipulator to move the surgical tool along the according to a first feed rate being required by the one or more controllers based on a surgical plan; and in response to the surgical tool being located on the target axis, control the robotic manipulator to move the surgical tool according to a second feed rate that is different from the first feed rate, the second feed rate being manually adjusted by interaction with the control interface integrated with the end effector.

In some implementations, the robotic manipulator comprises a plurality of links and a plurality of actuators configured to move the plurality of links, and the end effector coupled to a distal link of the plurality of links; the robotic manipulator further comprises a force/torque transducer that is coupled between the end effector and the distal link of the robotic manipulator and is configured to sense forces/torques externally applied to the end effector in six-degrees of freedom; the one or more controllers are configured to operate the robotic manipulator in a manual mode wherein the one or more controllers are configured to: evaluate external forces/torques externally applied to the end effector; determine a commanded position of the surgical tool along the target axis by evaluating the forces/torques are applied externally to the end effector; define a virtual boundary constraining movement of the surgical tool to the target axis; and enable movement of the surgical tool along the target axis to the commanded position; and the one or more controllers are further configured to control the robotic manipulator in a semi-autonomous mode wherein the robotic manipulator is configured to enable motorized movement of the surgical tool along the target axis free of operator assistance.

In some implementations, one or more controllers are configured to: define a first length of the target axis and a second length of the target axis; control the robotic manipulator to move the surgical tool along the first length of the target axis in the semi-autonomous mode; and control the robotic manipulator to move the surgical tool along the second length of the target axis in the manual mode.

In some implementations, one or more controllers are configured to: when the surgical tool is located off the target axis, control the robotic manipulator to move the surgical tool along the according the manual mode; and when the surgical tool is located on the target axis, control the robotic manipulator to move the surgical tool according to the semi-autonomous mode.

In some implementations, one or more sensors are further defined as one or more of the following: a sensor coupled to an actuator of the surgical tool and being configured to sense current draw of the actuator responsive to torque applied to the surgical tool by the bone structure; a sensor coupled to a guiding device, the guiding device configured to guide movement of the surgical tool towards the bone structure, the sensor being integrated or coupled to the guiding device; a pressure sensor coupled to the surgical tool and/or robotic manipulator and being configured to sense pressure applied to the surgical tool by the bone structure; a displacement sensor configured to sense displacement of the surgical tool relative to a reference point; and a depth sensor configured to sense depth of the surgical tool relative to a reference point.

In some implementations, the end effector comprises a grasping portion and the control interface is integrated with the grasping portion.

In some implementations, a navigation system configured to track a position of the end effector, and to store a virtual model of the bone structure, and wherein the target axis is defined relative to the virtual model.

A sixth aspect of the disclosure involves a method of operating the surgical system according to the fifth aspect of the disclosure, and optionally, according to any of the implementations within this section.

The fifth and sixth aspects of the disclosure are optionally implemented according to any of the implementations within this section.

A seventh aspect of the disclosure involves a surgical system configured for registration of a bone structure comprising an first cortical region comprising an anatomical landmark, the surgical system comprising: a surgical tool comprising a cutting bur rotatable about a cutting axis; a robotic manipulator comprising a plurality of links and joints and being configured to support and move the surgical tool; and one or more controllers being configured to control movement of one or more of the joints of the robotic manipulator and to control operation of the surgical tool, a navigation system configured to track an actual position of the cutting bur, and wherein: the one or more controllers are configured to control operation of the surgical tool to disable rotation of the cutting bur about the cutting axis and to control the robotic manipulator to cause the cutting bur to interact with the actual anatomical landmarks of the first cortical region; one or more sensors are configured to sense actual forces applied to the cutting bur by the actual anatomical landmarks of the first cortical region; and the one or more controllers are configured to: store a virtual model of the first cortical region comprising virtual anatomical landmarks of the first cortical region; store data correlating expected force measurements from the one or more sensors and expected positions of the cutting bur to the virtual anatomical landmarks of the first cortical region; receive measurements from the one or more sensors based on actual forces applied to the cutting bur by the actual anatomical landmarks of the first cortical region; receive actual position of the cutting bur from the navigation system; compare the actual force measurements from the one or more sensors and the actual position of the cutting bur from the navigation system with the expected force measurements and the expected positions of the cutting bur to associate the actual anatomical landmarks with one of the virtual anatomical landmarks of the first cortical region; and register the virtual model to the first cortical region based on association of the actual anatomical landmarks with one of the virtual anatomical landmarks of the first cortical region.

An eighth aspect of the disclosure involves a method of operating the surgical system according to the seventh aspect of the disclosure, and optionally, according to any of the implementations within this section.

The seventh and eighth aspects of the disclosure are optionally implemented according to any of the implementations within this section.

A ninth aspect of the disclosure involves a surgical system configured for manipulation of a bone structure comprising a cancellous bone region, the surgical system comprising: a surgical tool comprising a cutting bur rotatable about a cutting axis; a robotic manipulator comprising a plurality of links and joints and being configured to support and move the surgical tool; one or more sensors; and one or more controllers being configured to control movement of one or more of the joints of the robotic manipulator and to control operation of the surgical tool and to: advance the cutting bur through the cancellous bone region; using the one or more sensors, sense axial forces applied to the cutting bur by the cancellous bone region; compare the sensed axial forces to a predetermined axial force threshold defined to prevent displacement of the bone structure from axial force applied by the cutting bur; and adjust one or more of a rotational cutting speed of the cutting bur and a feed rate of the surgical tool to maintain advancement of the cutting bur through the cancellous bone region and to maintain the sensed axial forces below the axial force threshold.

A tenth aspect of the disclosure involves a method of operating the surgical system according to the ninth aspect of the disclosure, and optionally, according to any of the implementations within this section.

The ninth and tenth aspects of the disclosure are optionally implemented according to any of the implementations within this section.

These and other features will be more clearly understood from the following detailed description taken in conjunction with the accompanying drawings and claims.

For any of the aspects or implementations of the disclosure, the bone structure may be a vertebra. However, other types of bone structures that include cancellous bone are contemplated.

For any of the aspects or implementations of the disclosure, the entry point is a pedicle entry point and cannulation is for receipt of an implant, and the implant may be a pedicle screw. However, other types of entry points and implants are contemplated.

DETAILED DESCRIPTION

I. Overview

Referring to the Figures, wherein like numerals indicate like or corresponding parts throughout the several views, a surgical system 10 (hereinafter "system") and method for operating the system 10 are described herein and shown throughout the accompanying figures.

Figure 1:
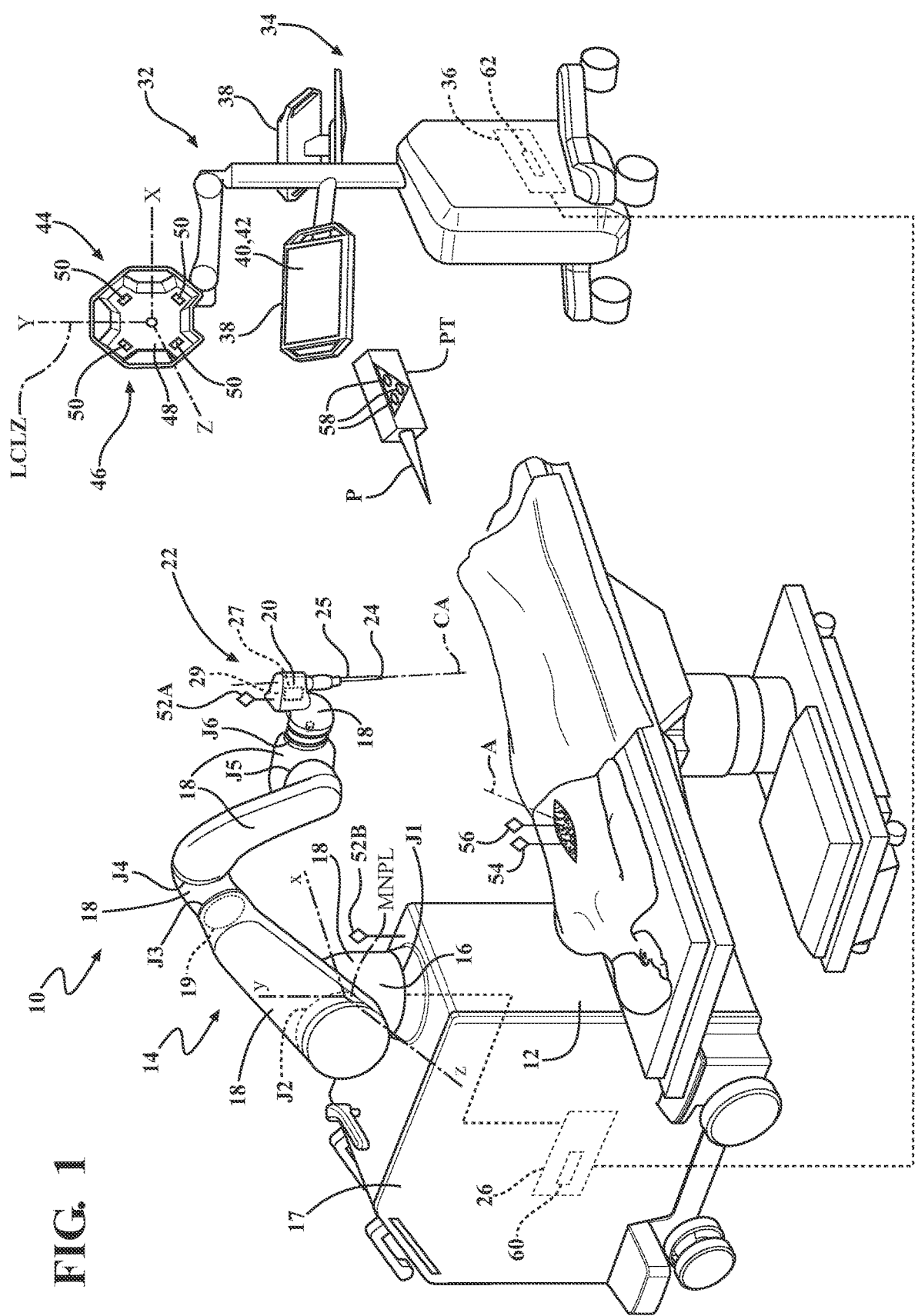
FIG. 1 is a perspective view of a robotic surgical system.

As shown in FIG. 1, the system 10 is a robotic surgical system for treating an anatomy (surgical site) of a patient 12, such as bone or soft tissue. In FIG. 1, the patient 12 is undergoing a surgical procedure. The anatomy in FIG. 1 includes a spine of the patient 12. The surgical procedure may involve tissue removal or treatment. In one aspect, the surgical procedure may involve planning and executing of cannulation of tissue and insertion of an implant within one or more bone structures. In one example, as primarily described herein, the bone structure is a vertebra of the spine. The techniques and advantages described herein, however are not limited only to vertebral bodies, and may be utilized for treating any bone structure, such as those having a cancellous bone region disposed between two cortical bone regions. Such bones may, for example, be in the limbs of the patient, and may include long bones, femurs, pelvic bones, ribs, the skull, or any other bone structure not described herein. The implant can be a pedicle screw when the bone structure is a vertebra. However, other types of implants are contemplated, and the disclosure is not limited solely to pedicle screw preparation.

The system 10 includes a manipulator 14. In one example, the manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1) or a parallel arm configuration. In other examples, more than one manipulator 14 may be utilized in a multiple arm configuration. The manipulator 14 comprises a plurality of joints (J) and a plurality of joint encoders 19 located at the joints (J) for determining position data of the joints (J). For simplicity, one joint encoder 19 is illustrated in FIG. 1, although it is to be appreciated that the other joint encoders 19 may be similarly illustrated. The manipulator 14 according to one example has six joints (J1-J6) implementing at least six-degrees of freedom (DOF) for the manipulator 14. However, the manipulator 14 may have any number of degrees of freedom and may have any suitable number of joints (J) and redundant joints (J). In one example, each of the joints (J) of the manipulator 14 are actively driven. In other examples, some joints (J) may be passively driven while other joints (J) are actively driven.

The base 16 of the manipulator 14 is generally a portion of the manipulator 14 that is stationary during usage thereby providing a fixed reference coordinate system (i.e., a virtual zero pose) for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference point, which does not move in the manipulator coordinate system MNPL. The manipulator 14 and/or manipulator cart 17 house a manipulator computer 26, or other type of control unit.

A surgical tool 20 (hereinafter "tool") couples to the manipulator 14 and is movable relative to the base 16 to interact with the anatomy. The tool 20 is or forms part of an end effector 22. The end effector 22 may be defined as the unit which attaches to the robotic manipulator 14. In one example, the end effector 22 attaches to a distal joint (J) of the manipulator 14. The tool 20 may be grasped by the operator. One exemplary arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference.

The tool 20 includes an energy applicator 24 designed to contact the tissue of the patient 12 at the surgical site. In some configurations, the energy applicator 24 is an accessory that can releasably attach to the tool 24. In alternative configurations, the energy applicator 24 is integrated with the tool 24 such that they are part of a common device. For at least this reason, descriptions of the tool 20 herein may apply fully to the energy applicator 24, and vice-versa, depending on the configuration of the tool 20 and energy applicator 24. For surgical procedures involving entry point creation and cannulation, the energy applicator 24 is preferably a cutting bur, and more specifically, a rotary cutting bur 24 (hereinafter referred to as "bur"). The bur 24 is rotatable about a cutting axis (CA), as shown in FIG. 1. Throughout this description, the energy applicator 24 is referred to as a bur. However, this should not be understood to limit the techniques herein solely to burs. The tool 20 can include a tool shaft 25, as shown in FIG. 1. A proximal end of the tool shaft 25 can be connected to a tool driver 27 that is driven by a tool motor 29, wherein the tool driver 27 and tool motor 29 are optionally included within a body of the end effector 22, as shown in FIG. 1, for example. The manipulator 14 and the tool 20, and components thereof, may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

Figure 12A:
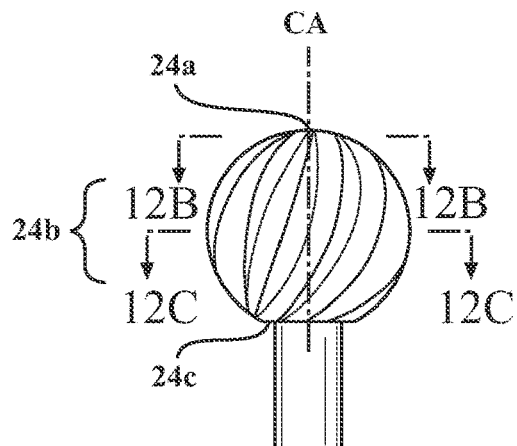
FIG. 12A-12C illustrates one example of a spherical bur suitable for some aspects of the disclosure related to creating a pedicle entry point and displacing and cannulating cancellous bone material with the bur.
Figure 12B:
Figure 12C:
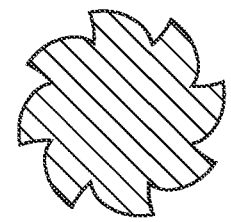
Figure 13:
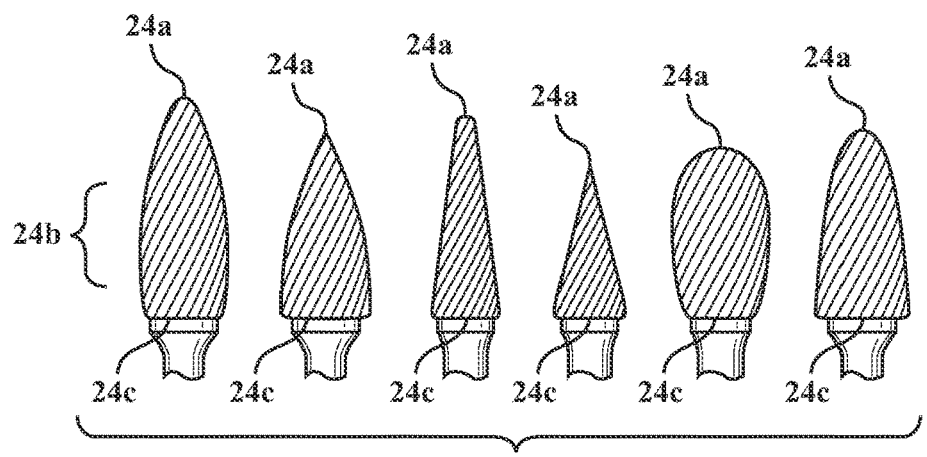
FIG. 13 illustrates various bur configurations with radius or pointed distal tips suitable for some aspects of the disclosure related to creating a pedicle entry point and displacing and cannulating cancellous bone material with the bur.

With reference to FIGS. 12 and 13, the bur 24 has a configuration that enables a multi-part functionality notable to certain aspects of the techniques described herein. Namely, the bur 24 comprises a distal cutting capacity enabling the bur 24 to cut at its distal tip along the cutting axis (CA), a side-cutting capacity enabling the bur 24 to cut laterally or transverse relative to the cutting axis (CA), as well as a radius and/or pointed tip to enable the bur 24 to efficiently and effectively push through spongy bone (e.g., cancellous bone material) without causing trauma or causing unintended displacement of the bone. The side cutting capacity of the bur 24 is noteworthy as this enables the bur 24 to cut into a cortical region of bone at an incidental surface, such as the angled surfaces of a pedicle region of a vertebra. With the side cutting capacity and techniques described herein, the bur 24 can avoid skiving.

In one example, the configuration enabling such functionality is a spherical bur 24, as shown in FIG. 12A-12C. Other examples of cutting burs 24 enabling such functionality are the burs (some of which are shown in FIG. 13) which may include a flame-shaped bur with radius and/or pointed end, tree-shaped bur with radius and/or pointed end, oval-shaped bur, cylinder-shaped bur with radius and/or pointed end, N-degree tapered bur with radius and/or pointed tip. Other types of burs other than those shown in FIGS. 12 and 13 are contemplated which meet the criteria described herein.

In any of the configurations of FIGS. 12 and 13, the cutting bur 24 comprises a distal tip 24a, a proximal portion 24c, and a peripheral portion 24c disposed or formed between the distal tip 24a and the proximal portion 24c. The distal 24a is usually, but not always, the first point of contact for the cutting bur 24 when the bur 24 approaches the target site along the cutting axis (CA). The proximal portion 24c is the portion where the cutting bur 24 cutting features are considered to end and transition into the tool shaft 25. The proximal portion 24c is opposite the distal tip 24a. The peripheral portion 24b is configured to cut in a direction lateral or transverse to the cutting axis (CA) to enable the cutting bur 24 to penetrate, e.g., the cortical region at a specific angled approach. As shown in FIG. 12B, the cross-sectional diameter of the distal tip 24a is less than a cross-sectional diameter of the peripheral portion 24b as shown in FIG. 12C. This narrowing of the cross-sectional diameter enables the bur 24 to efficiently and effectively push through spongy bone (e.g., cancellous bone material) without causing trauma or causing unintended displacement of the bone. The cross-section of the peripheral portion 24b can be taken anywhere along the cutting axis (CA) between the distal tip 24a and the proximal portion 24c and may be taken near a midpoint therebetween. The cross-section of the distal tip 24a may be taken within 1 mm of the distal-most point of the bur 24 or at any distal point that first produces a cross-sectional diameter.

Figure 14A:
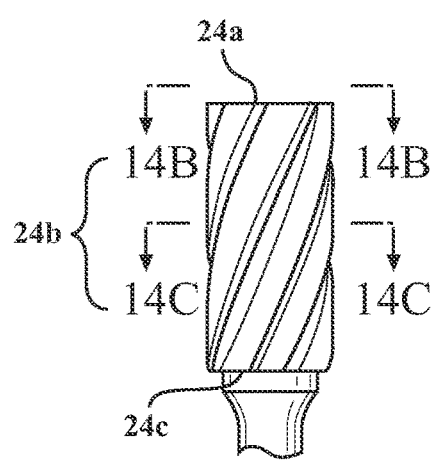
FIG. 14A-14C illustrate a cylindrical bur configuration distinguished from the bur configurations of FIGS. 12 and 13 wherein such bur configuration would not be suitable for the techniques described herein.
Figure 14B:
Figure 14C:
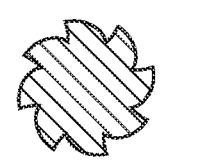

To the contrary, the example bur 24 in FIG. 14A-14C is not suitable for certain aspects of the techniques described herein. The peripheral portion 24b of the bur 24 of FIG. 14A may cut in a direction lateral or transverse to the cutting axis (CA) but the distal tip 24a is incapable of cutting in a direction along the cutting axis (CA) since the distal tip 24a is flat. As shown in FIG. 14B, the cross-sectional diameter of the distal tip 24a is the same as a cross-sectional diameter of the peripheral portion 24b (FIG. 14C), Hence, the flat distal tip 24a of FIG. 12C will create an undesirable amount of friction and force potentially destroying surrounding tissue and forcing unintended or undesirable movement of the bone. Similarly, typical cylindrical surgical drill bits are distinguished from cutting burs in that such drill bits lack side-cutting capacity for creating the entry point in cortical bone and such drill bits skive off the bone surface unless drilled in a direction normal to the surface. Furthermore, although a drill bit has been utilized to create a pilot hole, the drill bit is not suited for cannulation of the cancellous region, and hence, prior techniques typically require utilizing a different type of tool for cannulation. Also, typical probing structures, such as cannulas, stylets, needles, are distinguished from cutting burs in that such structures lack any cutting capacity, much less side-cutting capacity, for creating the entry point in cortical bone at incidental surface angles.

The tool 20 comprises a TCP, which in one example, is a predetermined reference point defined at the bur 24. The TCP has known position in its own coordinate system. The TCP may be located at any suitable portion of the bur 24, including at a center of gravity of the bur 24, a distal tip 24a, peripheral portion 24b, or proximal portion 24c of the bur 24. The TCP may relate to a bur having a specified diameter. In one example, when the bur 24 is spherical, the TCP is assumed to be located at the center of the sphere such that only one point may be tracked. The TCP may be defined according to various manners depending on the configuration of the bur 24. The TCP may also be located at a point along the shaft 25.

The robotic system, according to one aspect, is configured to prepare the anatomy for insertion of pedicle screws. Robotic systems, tools, and techniques for preparing for and installing pedicle screws can be like those described in U.S. patent application Ser. No. 16/184,376, filed Nov. 8, 2018, entitled "Robotic Spine Surgery System and Methods," the entire contents of which are hereby incorporated by reference.

Figure 2:
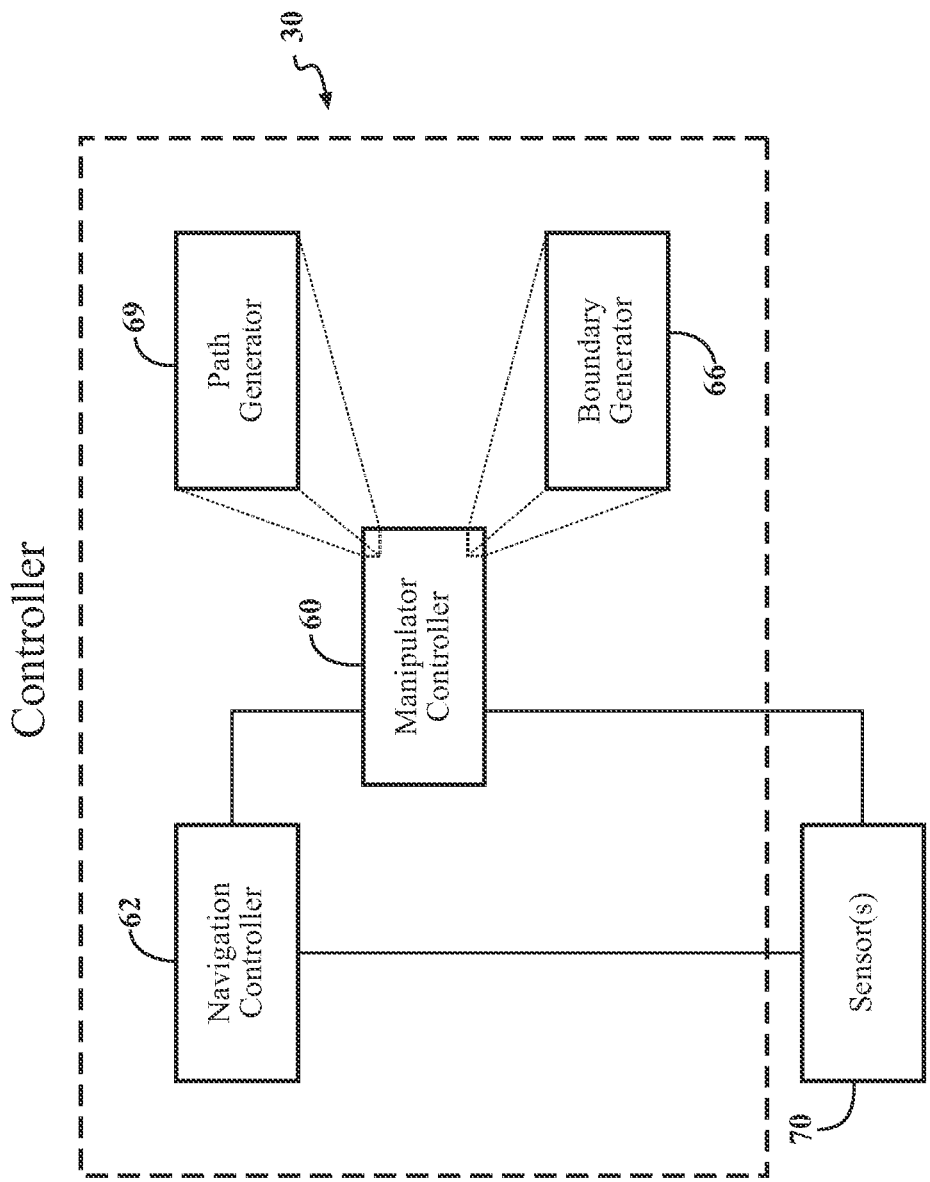
FIG. 2 is a block diagram of controllers of the robotic surgical system.

Referring to FIG. 2, the system 10 includes one or more controllers 30 (hereinafter referred to as "controller"). The controller 30 includes software and/or hardware for controlling the manipulator 14. The controller 30 directs the motion of the manipulator 14 and controls a state (position and/or orientation) of the tool 20 with respect to a coordinate system. In one example, the coordinate system is the manipulator coordinate system MNPL, as shown in FIG. 1. The manipulator coordinate system MNPL has an origin located at any suitable pose with respect to the manipulator 14. Axes of the manipulator coordinate system MNPL may be arbitrarily chosen as well. Generally, the origin of the manipulator coordinate system MNPL is defined at the fixed reference point of the base 16. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

As shown in FIG. 1, the system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 is configured to track movement of various objects. Such objects include, for example, the manipulator 14, the tool 20 and the anatomy, e.g., certain vertebrae or the pelvis of the patient. The navigation system 32 tracks these objects to gather state information of one or more of the objects with respect to a (navigation) localizer coordinate system LCLZ. Coordinates in the localizer coordinate system LCLZ may be transformed to the manipulator coordinate system MNPL, and/or vice-versa, using transformation techniques described herein.

The navigation system 32 includes a cart assembly 34 that houses a navigation computer 36, and/or other types of control units. A navigation interface is in operative communication with the navigation computer 36. The navigation interface includes one or more displays 38. The navigation system 32 is capable of displaying a graphical representation of the relative states of the tracked objects to the operator using the one or more displays 38. First and second input devices 40, 42 may be used to input information into the navigation computer 36 or otherwise to select/control certain aspects of the navigation computer 36. As shown in FIG. 1, such input devices 40, 42 include interactive touchscreen displays. However, the input devices 40, 42 may include any one or more of a keyboard, a mouse, a microphone (voice-activation), gesture control devices, head-mounted devices, and the like.

The navigation system 32 is configured to depict a visual representation of the anatomy and the tool 20 for visual guidance of any of the techniques described. The visual representation may be real (camera) images, virtual representations (e.g., computer models), or any combination thereof. The visual representation can be presented on any display viewable to the surgeon, such as the displays 38 of the navigation system 32, head mounted devices, or the like. The representations may be augmented reality, mixed reality, or virtual reality.

The navigation system 32 also includes a navigation localizer 44 (hereinafter "localizer") coupled to the navigation computer 36. In one example, the localizer 44 is an optical localizer and includes a camera unit 46. The camera unit 46 has an outer casing 48 that houses one or more optical sensors 50.

The navigation system 32 may include one or more trackers. In one example, the trackers include a pointer tracker PT, one or more manipulator trackers 52, one or more patient trackers 54, 56. In the illustrated example of FIG. 1, the manipulator tracker 52 is attached to the tool 20 (i.e., tracker 52A), the first patient tracker 54 is firmly affixed to a vertebra of the patient 12, and the second patient tracker 56 is firmly affixed to pelvis of the patient 12. In this example, the patient trackers 54, 56 are firmly affixed to sections of bone. The pointer tracker PT is firmly affixed to a pointer P used for registering the anatomy to the localizer coordinate system LCLZ. The manipulator tracker 52 may be affixed to any suitable component of the manipulator 14, in addition to, or other than the tool 20, such as the base 16 (i.e., tracker 52B), or any one or more links 18 of the manipulator 14. Those skilled in the art appreciate that the trackers 52, 54, 56, PT may be fixed to their respective components in any suitable manner.

When optical localization is utilized, however, one or more of the trackers may include active markers 58. The active markers 58 may include light emitting diodes (LEDs). Alternatively, the trackers 52, 54, 56 may have passive markers, such as reflectors, which reflect light emitted from the camera unit 46. Other suitable markers not specifically described herein may be utilized.

The localizer 44 tracks the trackers 52, 54, 56 to determine a state of one or more of the trackers 52, 54, 56, which correspond respectively to the state of the object respectively attached thereto. The localizer 44 provides the state of the trackers 52, 54, 56 to the navigation computer 36. In one example, the navigation computer 36 determines and communicates the state the trackers 52, 54, 56 to the manipulator computer 26. As used herein, the state of an object includes, but is not limited to, data that defines the position and/or orientation of the tracked object or equivalents/derivatives of the position and/or orientation. For example, the state may be a pose of the object, and may include linear data, and/or angular velocity data, and the like.

Although one example of the navigation system 32 is shown in the Figures, the navigation system 32 may have any other suitable configuration for tracking the manipulator 14 and the patient 12. The illustrated tracker configuration is provided merely as one example for tracking objects within the operating space. Any number of trackers may be utilized and may be located in positions or on objects other than shown. In other examples, such as described below, the localizer 44 may detect objects absent any trackers affixed to objects.

In one example, the navigation system 32 and/or localizer 44 are ultrasound-based. For example, the navigation system 32 may comprise an ultrasound imaging device coupled to the navigation computer 36. The ultrasound imaging device may be robotically controlled, or may be hand-held. The ultrasound imaging device images any of the aforementioned objects, e.g., the manipulator 14 and the patient 12, and generates state signals to the controller 30 based on the ultrasound images. The ultrasound images may be of any ultrasound imaging modality. The navigation computer 36 may process the images in near real-time to determine states of the objects. Ultrasound tracking can be performed absent the use of trackers affixed to the objects being tracked. The ultrasound imaging device may have any suitable configuration and may be different than the camera unit 46 as shown in FIG. 1. One example of an ultrasound tracking system can be like that described in U.S. patent application Ser. No. 15/999,152, filed Aug. 16, 2018, entitled "Ultrasound Bone Registration With Learning-Based Segmentation And Sound Speed Calibration," the entire contents of which are incorporated by reference herein.

In another example, the navigation system 32 and/or localizer 44 are radio frequency (RF)-based. For example, the navigation system 32 may comprise an RF transceiver coupled to the navigation computer 36. The manipulator 14 and the patient 12 may comprise RF emitters or transponders attached thereto. The RF emitters or transponders may be passive or actively energized. The RF transceiver transmits an RF tracking signal and generates state signals to the controller 30 based on RF signals received from the RF emitters. The navigation computer 36 and/or the controller 30 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52, 54, 56 as shown in FIG. 1.

In yet another example, the navigation system 32 and/or localizer 44 are electromagnetically based. For example, the navigation system 32 may comprise an EM transceiver coupled to the navigation computer 36. The manipulator 14 and the patient 12 may comprise EM components attached thereto, such as any suitable magnetic tracker, electromagnetic tracker, inductive tracker, or the like. The trackers may be passive or actively energized. The EM transceiver generates an EM field and generates state signals to the controller 30 based upon EM signals received from the trackers. The navigation computer 36 and/or the controller 30 may analyze the received EM signals to associate relative states thereto. Again, such navigation system 32 examples may have structural configurations that are different than the navigation system 32 configuration as shown throughout the Figures.

In yet another example, the navigation system 32 and/or localizer 44 utilize a machine vision system which includes a video camera coupled to the navigation computer 36. The video camera is configured to locate a physical object in a target space. The physical object has a geometry represented by virtual object data stored by the navigation computer 36. The detected objects may be tools, obstacles, anatomical features, trackers, or the like. The video camera and navigation computer 36 are configured to detect the physical objects using image processing techniques such as pattern, color, or shape recognition, edge detection, pixel analysis, neutral net or deep learning processing, optical character recognition, barcode detection, or the like. The navigation computer 36 can compare the captured images to the virtual object data to identify and track the objects. A tracker may or may not be coupled to the physical object. If trackers are utilized, the machine vision system may also include infrared detectors for tracking the trackers and comparing tracking data to machine vision data. Again, such navigation system 32 examples may have structural configurations that are different than the navigation system 32 configuration as shown throughout the Figures. Examples of machine vision tracking systems can be like that described in U.S. Pat. No. 9,603,665, entitled "Systems and Methods for Establishing Virtual Constraint Boundaries" and/or like that described in U.S. Provisional Patent Application No. 62/698,502, filed Jul. 16, 2018, entitled "Systems and Method for Image Based Registration and Calibration," the entire contents of which are incorporated by reference herein.

The navigation system 32 and/or localizer 44 may have any other suitable components or structure not specifically recited herein. Furthermore, any of the techniques, methods, and/or components described above with respect to the camera-based navigation system 32 shown throughout the Figures may be implemented or provided for any of the other examples of the navigation system 32 described herein. For example, the navigation system 32 may utilize solely inertial tracking or any combination of tracking techniques.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include instructions stored in one or more non-transitory computer readable medium or memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules. The user interface software may run on a separate device from the manipulator computer 26 and navigation computer 36.

The controller 30 includes a manipulator controller 60 for processing data to direct motion of the manipulator 14. In one example, as shown in FIG. 1, the manipulator controller 60 is implemented on the manipulator computer 26. The manipulator controller 60 may receive and process data from a single source or multiple sources. The controller 30 further includes a navigation controller 62 for communicating the state data relating to the anatomy to the manipulator 14 to the manipulator controller 60. The manipulator controller 60 receives and processes the state data provided by the navigation controller 62 to direct movement of the manipulator 14. In one example, as shown in FIG. 1, the navigation controller 62 is implemented on the navigation computer 36. The manipulator controller 60 or navigation controller 62 may also communicate states of the patient 12 and manipulator 14 to the operator by displaying an image of the anatomy and the manipulator 14 on the one or more displays 38. The manipulator computer 26 or navigation computer 36 may also command display of instructions or request information using the display 38 to interact with the operator and for directing the manipulator 14.

The one or more controllers 30, including the manipulator controller 60 and navigation controller 62, may be implemented on any suitable device or devices in the system 10, including, but not limited to, the manipulator computer 26, the navigation computer 36, and any combination thereof. As will be described herein, the controller 30 is not limited to one controller, but may include a plurality of controllers for various systems, components or sub-systems of the surgical system 10. These controllers may be in communication with each other (e.g., directly or indirectly), and/or with other components of the surgical system 10, such as via physical electrical connections (e.g., a tethered wire harness) and/or via one or more types of wireless communication (e.g., with a WiFi™ network, Bluetooth®, a radio network, and the like). Any of the one or more controllers 30 may be realized as or with various arrangements of computers, processors, control units, and the like, and may comprise discrete components or may be integrated (e.g., sharing hardware, software, inputs, outputs, and the like). Any of the one or more controllers may implement their respective functionality using hardware-only, software-only, or a combination of hardware and software. Examples of hardware include, but is not limited, single or multi-core processors, CPUs, GPUs, integrated circuits, microchips, or ASICs, digital signal processors, microcontrollers, field programmable gate arrays, systems on a chip, discrete circuitry, and/or other suitable hardware, and the like. The one or more controllers may implement software programs, software modules, algorithms, logical rules, look-up tables and other reference data, and various software layers for implementing any of the capabilities described herein. Equivalents of the software and hardware for the one or more controllers 30, and peripheral devices connected thereto, are fully contemplated.

As shown in FIG. 2, the controller 30 includes a boundary generator 66. The boundary generator 66 is a software module that may be implemented on the manipulator controller 60. Alternatively, the boundary generator 66 may be implemented on other components, such as the navigation controller 62. The boundary generator 66 generates virtual boundaries (VB) for constraining the tool 20 and/or bur 24. Such virtual boundaries (VB) may also be referred to as virtual meshes, virtual constraints, line haptics, or the like. The virtual boundaries (VB) may be defined with respect to a 3-D bone model registered to the one or more patient trackers 54, 56 such that the virtual boundaries (VB) are fixed relative to the bone model. The state of the tool 20 and/or bur 24 is tracked relative to the virtual boundaries (VB). In one example, the state of the TCP is measured relative to the virtual boundaries (VB) for purposes of determining when and where haptic feedback force is applied to the manipulator 14, or more specifically, the tool 20 and/or bur 24.

A tool path generator 68 is another software module run by the controller 30, and more specifically, the manipulator controller 60. The tool path generator 68 generates a path for the tool 20 and/or bur 24 to traverse, such as for removing sections of the anatomy to receive an implant. One exemplary system and method for generating the tool path is explained in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries (VB) and/or tool paths may be generated offline rather than on the manipulator computer 26 or navigation computer 36. Thereafter, the virtual boundaries (VB) and/or tool paths may be utilized at runtime by the manipulator controller 60.

Additionally, it may be desirable to control the manipulator 14 in different modes of operation for the system 10. For example, the system 10 may enable the manipulator 14 to interact with the site using manual and semi-autonomous modes of operation. An example of the semi-autonomous mode is described in U.S. Pat. No. 9,119,655, entitled, "Surgical Manipulator Capable of Controlling a Surgical Instrument in Multiple Modes," the disclosure of which is hereby incorporated by reference. In the semi-autonomous mode, the manipulator 14 directs movement of the tool 20 and, in turn, the bur 24 at the surgical site. In one instance, the controller 30 models the tool 20 and/or bur 24 as a virtual rigid body and determines forces and torques to apply to the virtual rigid body to advance and constrain the tool 20 and/or bur 24 along any trajectory or path in the semi-autonomous mode. Movement of the tool 20 in the semi-autonomous mode is constrained in relation to the virtual constraints generated by the boundary generator 66 and/or path generator 69, In the semi-autonomous mode, the manipulator 14 is capable of moving the tool 20 free of operator assistance. Free of operator assistance may mean that an operator does not physically move the tool 20 by applying external force to move the tool 20. Instead, the operator may use some form of control to manage starting and stopping of movement. For example, the operator may hold down a button of a control to start movement of the tool 20 and release the button to stop movement of the tool 20. Alternatively, the operator may press a button to start movement of the tool 20 and press a button to stop motorized movement of the tool 20 along the trajectory or path. The manipulator 14 uses motorized movement to advance the tool 20 in accordance with pre-planned parameters.

Alternatively, the system 10 may be operated in the manual mode. Here, in one instance, the operator manually directs, and the manipulator 14 controls, movement of the tool 20 and, in turn, the bur 24 at the surgical site. The operator physically contacts the tool 20 to cause movement of the tool 20. The manipulator 14 monitors the forces and torques placed on the tool 20 by the operator in order to position the tool 20. A sensor that is part of the manipulator 14, such as a force-torque transducer, measures these external forces and torques applied to the manipulator 14 and/or tool 20, e.g., in six degrees of freedom. In one example, the sensor is coupled between the distal-most link of the manipulator (J6) and the end effector. In response to the applied forces and torques, the one or more controllers 30, 60, 62 are configured to determine a commanded position of the tool 20 by evaluating the forces/torques applied externally to the end effector with respect to virtual model of the bur 24 and/or surgical tool 20 in a virtual simulation. The manipulator 14 then mechanically moves the tool 20 to the commanded position in a manner that emulates the movement that would have occurred based on the forces and torques applied externally by the operator. Movement of the tool 20 in the manual mode is also constrained in relation to the virtual constraints generated by the boundary generator 66 and/or path generator 69.

II. Robotic Techniques for Cortical Bone Penetration and Cancellous Bone Cannulation The below techniques address potential deficiencies in robotic surgical accuracy involved with cortical bone penetration and cancellous bone cannulation and circumvent potential errors that might later occur during robotic pedicle implant placement. Additionally, the techniques described herein further provides a supplement or replacement to surgeon skill needed for achieving clinically acceptable accuracy. For example, the system 10 can provide robotic assistance for purposes such as detecting sensitive walls of the bone structure and avoiding breach thereof, controlling cannulation provided by the tool 20 and/or bur 24 for providing a more anatomically correct path within the bone structure for implant insertion, anticipating and detecting skiving of the tool 20 and/or bur 24 at the entry point of the bone structure, providing robotically controlled biasing of the entry point of the tool 20 and/or bur 24 by restoring motion of the tool 20 and/or bur 24 against the skiving direction, and providing advanced control hardware and techniques for feed rate advancement relative to the regions of the bone structure.

The techniques herein also provide robotic execution of cannulation with high accuracy in order to precisely position and advance the tool 20 and/or bur 24 within the bone structure while avoiding a breach at inner cortical walls, thereby mitigating potential nerve injury.

The techniques herein provide technical robotic solutions to address the practical reality that there is inherently some mechanical compliance with the cancellous bone region of a bone structure. In other words, the solutions address situations where the tool 20 and/or bur 24 can shift off a target axis within the cancellous bone region. The techniques provide technical robotic solutions to avoid the tool 20 and/or bur 24 from causing inadvertent movement of the bone structure by applying excessive force to the same.

The techniques herein also provide solutions that enable robotically and actively controlled cortical region penetration and cancellous bone cannulation as compared with prior techniques which are manually performed by the hand of the surgeon using hand-held tools or using manual tools within a robotic guide tube. The techniques herein also provide solutions that improve surgical efficiency by utilizing, in some instance, the same robotic system and the same cutting bur for cortical region penetration and cancellous bone cannulation. Hence, this avoids the need to utilize and/or exchange various tools for various parts of the procedure.

Within this section, the bone structure primarily described is a vertebra of the spine. The techniques and advantages described herein, however are not limited only to vertebral bodies, and may be utilized for treating any bone structure having a cancellous bone region disposed between two cortical bone regions. Such bones may, for example, be in the limbs of the patient, and may include long bones, femurs, pelvic bones, ribs, skull, or any other bone structure not described herein. Furthermore, the examples below address preparation for pedicle screw placement, for example, as part of spinal fusion. However, other types of cancellous bone preparation and implants are contemplated, and the disclosure is not limited solely to pedicle screw preparation for spinal procedures. Any of the description provided herein relative to the vertebra, its cortical cancellous regions, and operation of the system 10 can be fully applied to other types of similar bones.

As shown throughout FIGS. 3-11, the bone structure comprises first cortical region (CR1), a second cortical region (CR2), and a cancellous bone region (CBR) disposed between the first and second cortical regions (CR1, CR2). The first cortical region (CR1) is a region of the bone structure that the tool 20 and/or bur 24 usually interacts with or contacts first. Typically, this the exterior region of the bone that is exposed during surgery. However, the first cortical region (CR1) typically also comprises an interior surface that is not exposed during surgery as it is obscured by the exterior surface of the bone structure. The second cortical region (CR2) may, but not always, be integrally formed with the first cortical region (CR2). For example, assuming the bone is a hollow volume (such as a hollow cylinder), the first cortical region (CR1) and the second cortical region (CR2) may be the opposing walls of the volume encasing the hollow region. The second cortical region (CR2) is typically obscured by the first cortical region (CR2) and cancellous bone region (CBR). The cancellous bone region (CBR) is typically encapsulated by the first and second cortical regions (CR1, CR2).

The cortical regions (CR1, CR2) are understood in the medical and surgical field to mean the hard, rigid, and compact form of connective tissue constituting skeletal bone, composed chiefly of calcium salts. The cortical regions (CR1, CR2) have a porosity typically ranging between 5% and 10%. The cancellous bone region (CBR) is also understood in the medical and surgical field as spongy or trabecular bone that is light, porous bone enclosing numerous large spaces that give a honeycombed or spongy appearance. The bone framework is organized into a three-dimensional latticework of bony processes, called trabeculae, arranged along lines of stress. The spaces between are often filled with marrow and blood vessels. The cancellous bone region (CBR) is much more porous than the cortical regions (CR1, CR2) with porosity ranging anywhere from 50% to 90%. The cortical regions (CR1, CR2) provide greater strength and rigidity to the bone structure, while the open structure of cancellous bone region (CBR) enables the bone structure to dampen stresses.

The tool 20 and/or bur 24 can penetrate the softer cancellous bone region (CBR) more easily than the harder cortical regions (CR1, CR2). The tool 20 and/or bur 24 may interact with multiple surfaces or layers of the first and second cortical regions (CR1, CR2) and cancellous bone region (CBR). For instance, the tool 20 and/or bur 24 may interact with the exterior surface of either of the first and second cortical regions (CR1, CR2), where the exterior surface is understood as the exterior cortical surface of the bone structure. Additionally, or alternatively, the tool 20 and/or bur 24 may interact with an interior surface of either of the first and second cortical regions (CR1, CR2), where the interior surface is understood as the interior cortical surface within the bone structure that is directly adjacent to the cancellous bone region (CBR). The tool 20 and/or bur 24 may also interact with any portion of the cancellous bone region (CBR) between the first and second cortical regions (CR1, CR2). The above possibilities are contemplated for any of the techniques described herein.

A. Robotic Techniques for Cannulation and Avoidance of Inner Cortical Wall Breach Described herein are techniques for utilizing the robotic manipulator 14 for interacting with the vertebra (V) of the patient, and more specifically, for cannulating the vertebra (V) in preparation for pedicle screw insertion. Once again, the vertebra (V) is only one example of a bone structure that can be subjected to these techniques.

To facilitate the techniques described herein, the surgical system 10 may be configured with one or more sensors 70 (FIG. 2) configured to sense forces applied to the tool 20 and/or bur 24, wherein the forces are applied by the vertebra (V) during interaction of the surgical tool and/or bur 24 to with the vertebra (V). These forces may be in response to interaction with any component of the bone structure, including the cancellous bone region (CBR) and the first and second cortical regions (CR1, CR2).

For any of the examples described herein, the forces sensed may include lateral or axial forces applied to the tool 20 and/or bur 24 as well as any lateral or axial torques applied to the tool 20 and/or bur 24. Furthermore, the sensed forces may be sensed as applied to the TCP of the tool 20 and/or bur 24, but may be sensed at other regions or points of the tool 20 and/or bur 24. As will be appreciated below, the sensors 70 can sense forces applied to the tool 20 and/or bur 24 by external or internal features of the vertebra (V).

The one or more sensors 70 can have various configurations. For example, the sensor 70 can be coupled to the robotic manipulator 14, and more specifically, to an actuator of the tool 20 and/or bur 24. The sensor 70 is configured to sense electrical current draw of the actuator responsive to torque applied to the tool 20 and/or bur 24 by the vertebra (V). The torque is applied due to contact of the bur 24 during rotation thereof, for example, during milling tissue of the vertebra.

In another example, the sensor 70 is coupled to a guiding device configured to guide movement of the tool 20 and/or bur 24 towards the vertebra (V). The guiding device can be coupled to the tool 20 and/or coupled to the patient. The guiding device can be a guide tube for guiding the tool 20 along an axis towards the vertebra (V). The guiding device can have other configurations for guiding the tool 20. The sensor 70 is integrated or coupled to the guiding device. The sensor 70 can be an inertial sensor, pressure sensor, strain gage or load cell, magnetic sensor, etc. Signals from the sensor 70 can be transmitted to the controller 30 using any suitable technique, such as transmission through the navigation system 32 using optical or wireless communication, or the like.

In another example, the sensor 70 is a pressure sensor coupled to the tool 20 and/or robotic manipulator 14 and is configured to sense pressure applied to the tool 20 and/or bur 24 by the vertebra (V). The pressure sensor can be integrated into the bur 24 or may be configured to the shaft 25 of the tool 20.

In another example, the sensor 70 is a displacement sensor or depth sensor configured to sense displacement/depth of the tool 20 and/or bur 24 relative to a reference point. The reference point may be defined pre-operatively or intraoperatively and may be stored by the navigation system 32. The reference point may be a virtual point or a physical point corresponding to a physical landmark or feature. The reference point may also be stored relative to a virtual model of the vertebra (V). The reference point may also be tracked by the navigation system 32. In one example, the navigation system 32 functions as the displacement or depth sensor by tracking the position of the bur 24 relative to the reference point. In other examples, the displacement/depth sensor may be coupled to a guiding device, such as the guide tube described above, for sensing displacement or depth of the tool 20 relative to the guiding device. In other examples, the displacement sensor is coupled to the tool 20 and/or robotic manipulator 14 and is configured to sense axial or lateral displacement of the tool 20 and/or bur 24 in response to contact with the vertebra (V). Depth of displacement can also be determined by determining the position of the tool 20 by analyzing the kinematic data (e.g., joint angles or positions) of the robotic manipulator 14.

In other examples, the sensor 70 is an inertial sensor, such as an accelerometer, gyroscope, magnetometer, inclinometer, or the like. These inertial sensors 70 can be affixed to the patient, to the tool 20, to the robotic manipulator 14, and/or to guiding devices for passively directing tool 20 motion.

In yet another example, as shown in FIG. 6, the sensor 70 is further defined as a force/torque transducer 72 that is coupled between the end effector/tool 20 and the bur 24. The force/torque transducer 72 is configured to sense forces/torques applied to the bur 24 by the vertebra in six-degrees of freedom.

The one or more sensors 70 may also be a combination of any of the sensors described above. Furthermore, the one or more sensors may have configurations other than described above.

The one or more controllers 30, 60, 62 analyze measurements from the one or more sensors 70 produced in response to interaction of the tool 20 and/or bur 24 with the vertebra (V). In response, the one or more controllers 30, 60, 62 control the robotic manipulator 14 and/or the tool 20, including the bur 24. The various techniques for controlling the robotic manipulator 14 and/or the tool 20 responsive to are described below.

In one example, the one or more controllers 30, 60, 62 are configured to control the robotic manipulator 14 and/or tool 20 to reduce forces applied to the tool 20 (or bur 24) by the vertebra.

Cannulation for pedicle screw insertion involves preparation of a pilot hole within the pedicle of the vertebra, wherein the pedicle is one example of the first cortical region (CR1). The second cortical region (CR2) is can more specifically be defined as the interior surface of the medial cortex of the vertebra (V) or any lateral, inferior, or superior cortical margin. However, the techniques described herein can be utilized with different regions of cortical and cancellous tissue other than those found in a vertebra. The forces applied to the tool 20 may be applied by any of these regions. Forces are detected for purposes, such as avoiding contact or breach of the second cortical region (CR2) by the tool 20 and/or bur 24. The techniques described herein ensure that the tool 20 and/or bur 24 manipulate the cancellous bone region (CBR) for cannulation by being bound by the surrounding cortical regions of the pedicle without breaching the same.

The one or more controllers 30, 60, 62 are configured to control the robotic manipulator 14 and/or tool 20 to reduce forces applied to the tool 20 (or bur 24) by the vertebra in response to the tool 20 interacting with the first cortical region (CR1) of the vertebra.

Figure 3A:
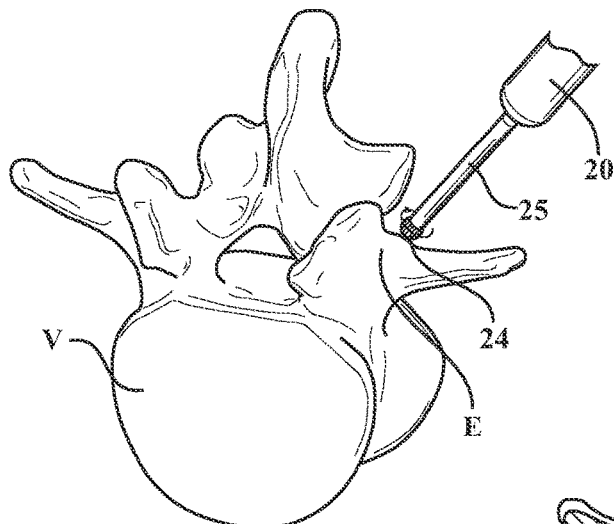
FIGS. 3A-3D illustrate progressive movement of a tool of the robotic surgical system advanced relative to regions of a vertebra in a cutting mode for pedicle cannulation, ultimately resulting in an error condition shown in FIG. 3D wherein the tool breaches an inner cortical region.

In FIG. 3A, the one or more controllers 30, 60, 62 are configured to move the tool 20 and/or bur 24 towards the first cortical region (CR1) and to enable energization of the bur 24 for penetration of the first cortical region (CR1). The penetration can be an entry point (E) predefined according to a surgical plan. In one example, the entry point (E) is located on the pedicle at the intersection of the transverse process and the line connecting two facet joints.

Figure 3B:
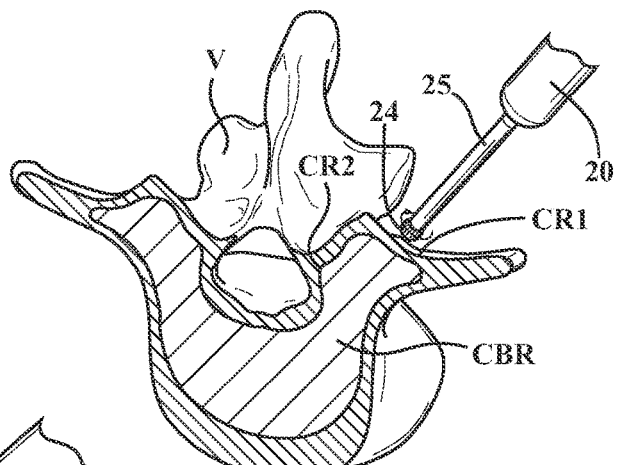

With reference to FIG. 3B, the entry point (E) can be manually approached using the skill of the surgeon. The tool 20 and/or bur 24 can be constrained by the robotic manipulator 14 according to a virtual boundary (VB) or line haptic wherein the tool 20 and/or bur 24 is moved in the manual mode towards the entry point (E). Alternatively, the robotic manipulator 14 can semi-autonomously reach the entry point (E) absent direct assistance from the user applying forces to the robotic manipulator 14.

Figure 3C:
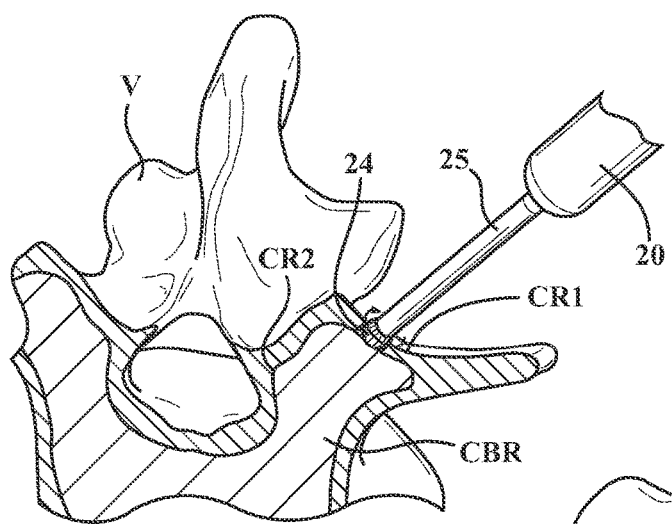

In FIG. 3C, the tool 20 and/or bur 24 actively burrs the first cortical region (CR1) at high speeds until the bur 24 breaches the same and enters the cancellous bone region (CBR). As will be described below, this transition from the first cortical region (CR1) to the cancellous bone region (CBR) can be sensed by the one or more sensors 70. The tool 20 and/or bur 24 is advanced through the cancellous bone region (CBR) by the robotic manipulator 14. During this advancement, the one or more sensors 70 can continue to sense forces applied to the tool 20 and/or bur 24 by the cancellous bone region (CBR).

As the tool 20 and/or bur 24 advances through the cancellous bone region (CBR), the tool 20 and/or bur 24 can be driven in cutting mode (as shown) and can eventually contact the second cortical region (CR2). The one or more sensors 70 can sense forces applied to the tool 20 and/or bur 24 by the second cortical region (CR2). In some instances, the sensors 70 can sense an anticipated contact between the tool 20 and/or bur 24 and the second cortical region (CR2) before such contact occurs. The one or more controllers 30, 60, 62 control the robotic manipulator 14 and/or tool 20 to reduce forces applied to (or forces soon to be applied to) the tool 20 and/or bur 24 by the second cortical region (CR2).

Figure 3D:
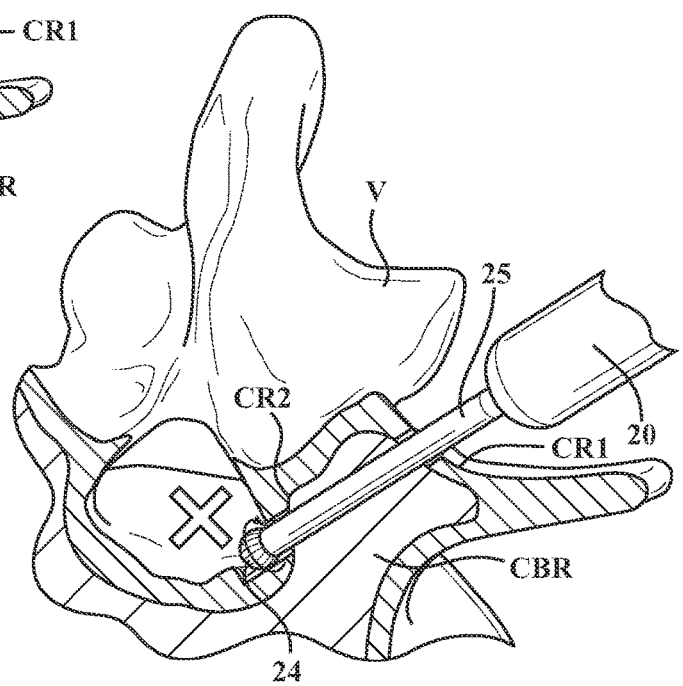

FIG. 3D depicts an error condition wherein the bur 24, while remaining in a cutting mode, inadvertently breaches the second cortical region (CR2). This error condition is mitigated using the techniques described herein.

Figure 4:
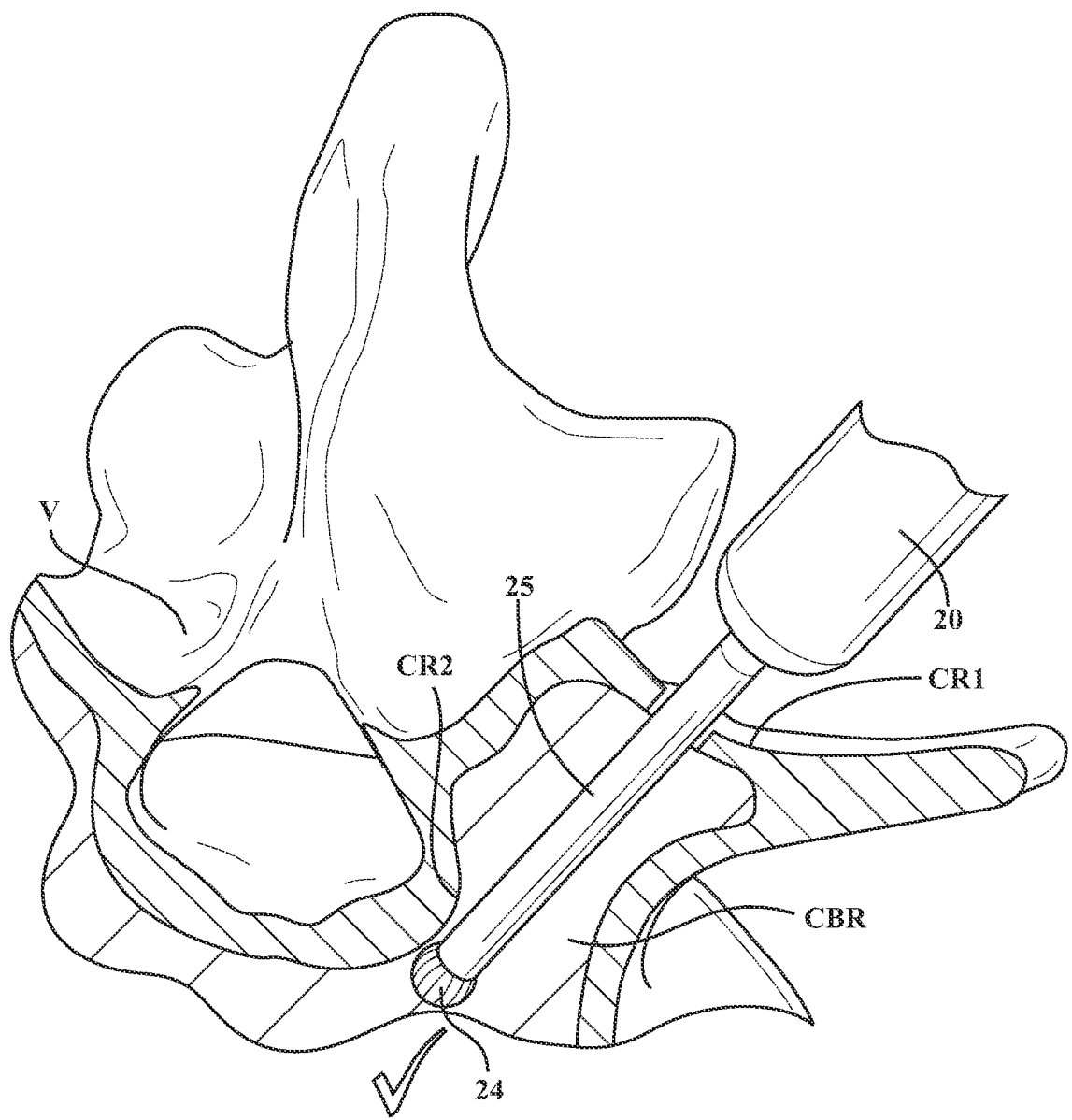
FIG. 4 illustrates one example of a desirable outcome wherein the tool is advanced through an outer cortical region and a cancellous bone region of the vertebra for cannulation while avoiding breach of the inner cortical region of the vertebra.

The more anatomically correct method for pedicle cannulation avoids breach of the second cortical region (CR2), and is shown in FIG. 4. The techniques described herein are provided in furtherance of achieving this preferable clinical outcome.

Reducing forces applied to the tool 20 and/or bur 24 by the second cortical region (CR2) can be executed in various manners. In one example, the robotic manipulator 14 is configured to adjust a trajectory of the tool 20 and/or bur 24 to reduce contact between the tool 20 and/or bur 24 and the second cortical region (CR2). For example, as shown in FIGS. 5A-5C, and FIGS. 6A-6B, the robotic manipulator 14 can move the cutting axis (CA) of the tool 20 and/or bur 24 off the target axis (A, TA) along which the tool 20 and/or bur 24 originally entered the vertebra (V). The cutting axis (CA) of the tool 20 and/or bur 24 can be shifted off the target axis (TA) while the bur 24 is within the cancellous bone region (CBR) because the cancellous bone region (CBR) is spongy and less dense than the first cortical region (CR1). The cutting axis (CA) of the tool 20 and/or bur 24 can be controllably shifted away from the second cortical region (CR1) to reduce forces applied by the second cortical region (CR2) and avoid breach of the same.

Figure 6A:
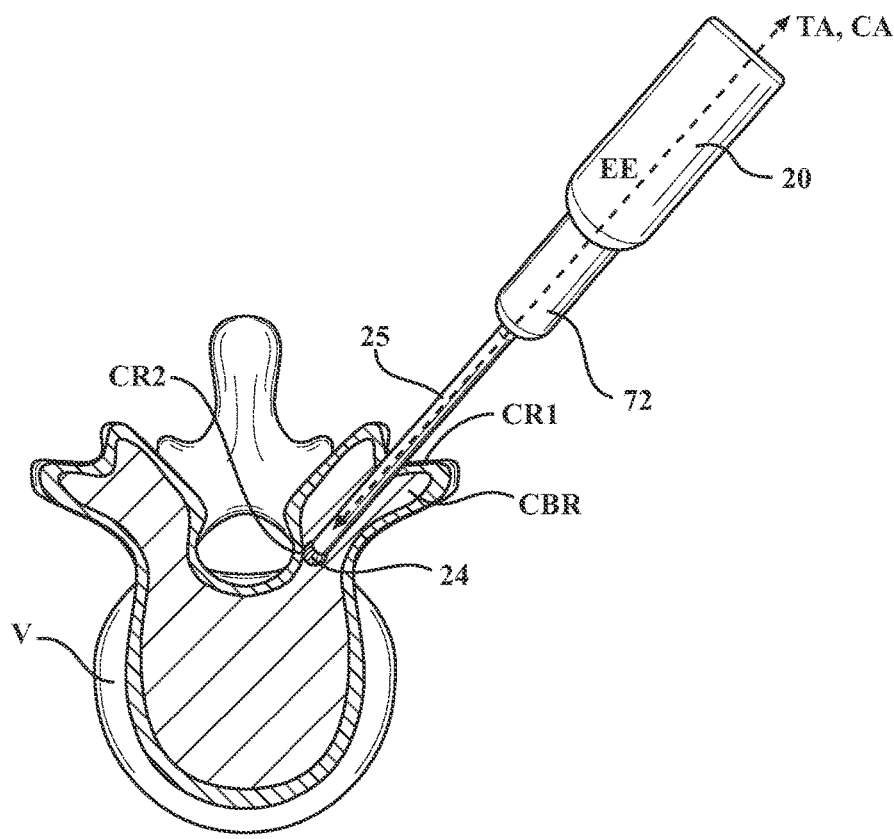
FIGS. 6A-6B illustrate an example wherein a force/torque sensor is provided between a distal end of the tool and an end effector of the robotic surgical system, and wherein the sensor detects forces applied to the tool by the inner cortical wall (FIG. 6A) and, in response, the surgical system adjusts a trajectory of the tool to avoid breach of the inner cortical region (FIG. 6B)
Figure 6B:
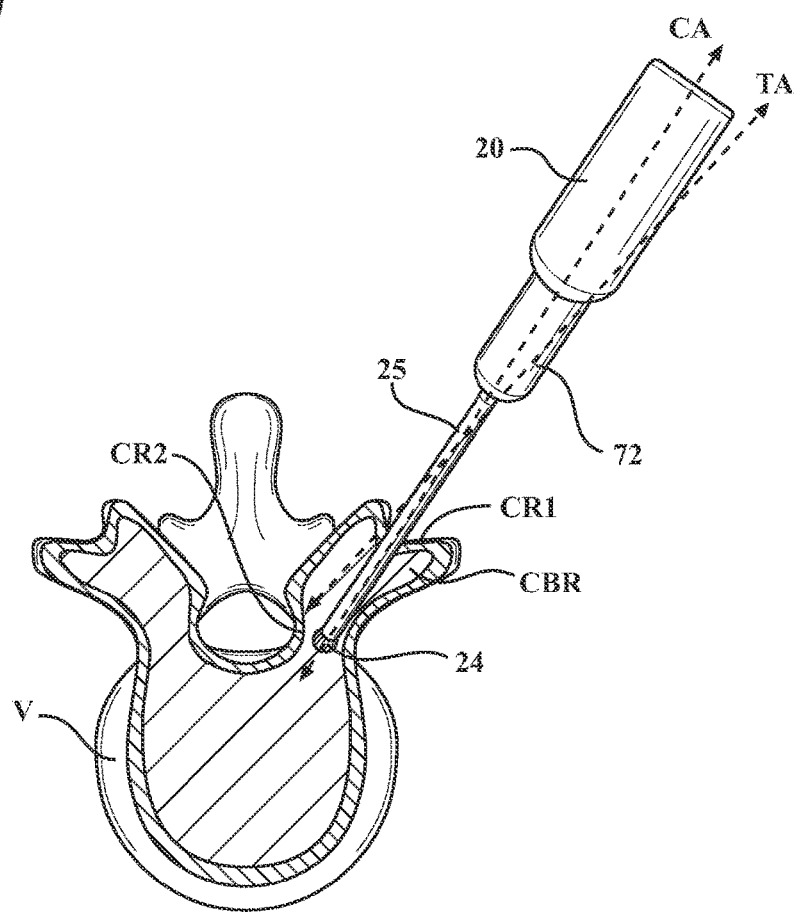

In FIG. 6A, the force torque sensor 72 employed between the bur 24 and the surgical tool 20 (or end effector body) is utilized to detect forces applied by the second cortical region (CR2). In FIG. 6B, the trajectory of the tool 20 and/or bur 24 is actively controlled to be oriented away from the second cortical region (CR2) in response to detected forces from the sensor 72 sent back to the one or more controllers 30, 60, 62.

Figure 5A:
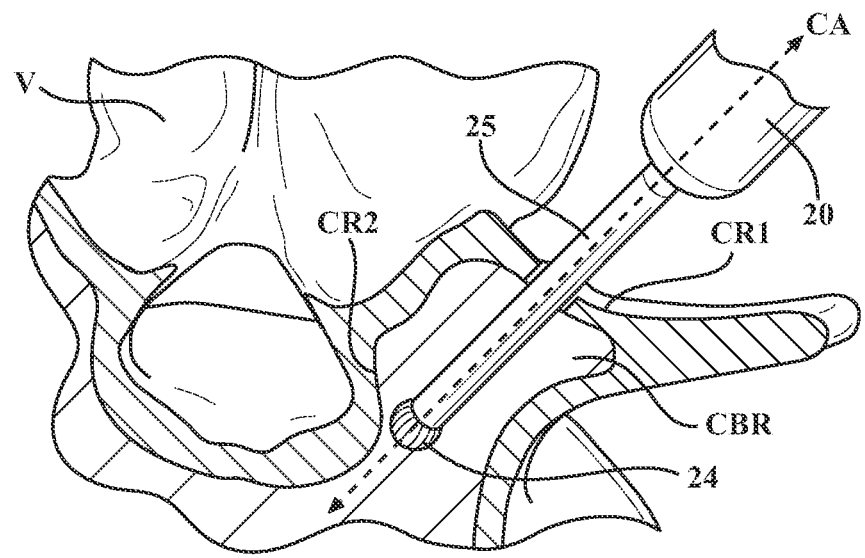
FIGS. 5A-5C illustrate progressive movement of the tool through the regions of the vertebra for cannulation, wherein the surgical system is configured to adjust a trajectory of the tool to avoid breach of the inner cortical region.
Figure 5B:
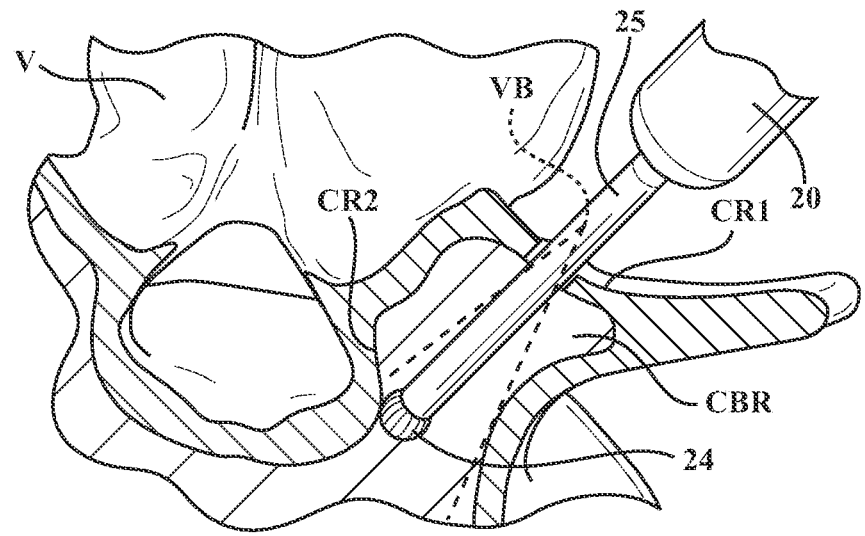
Figure 5C:
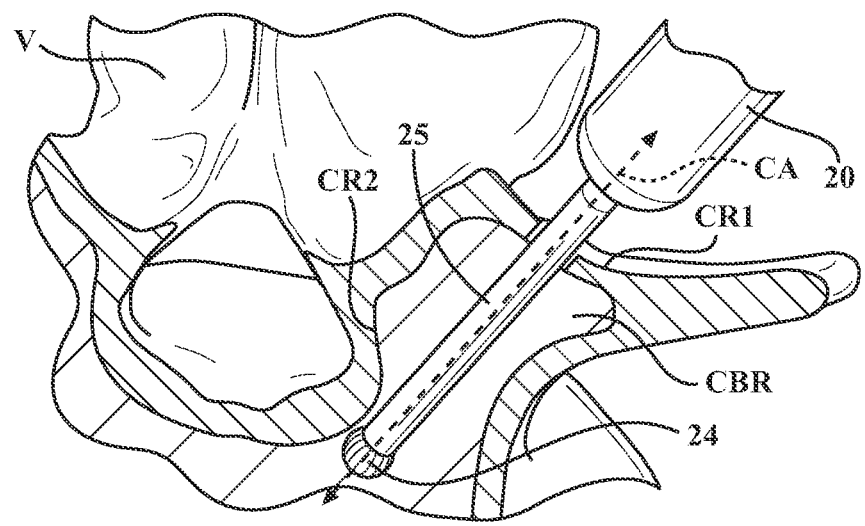
Figure 8:
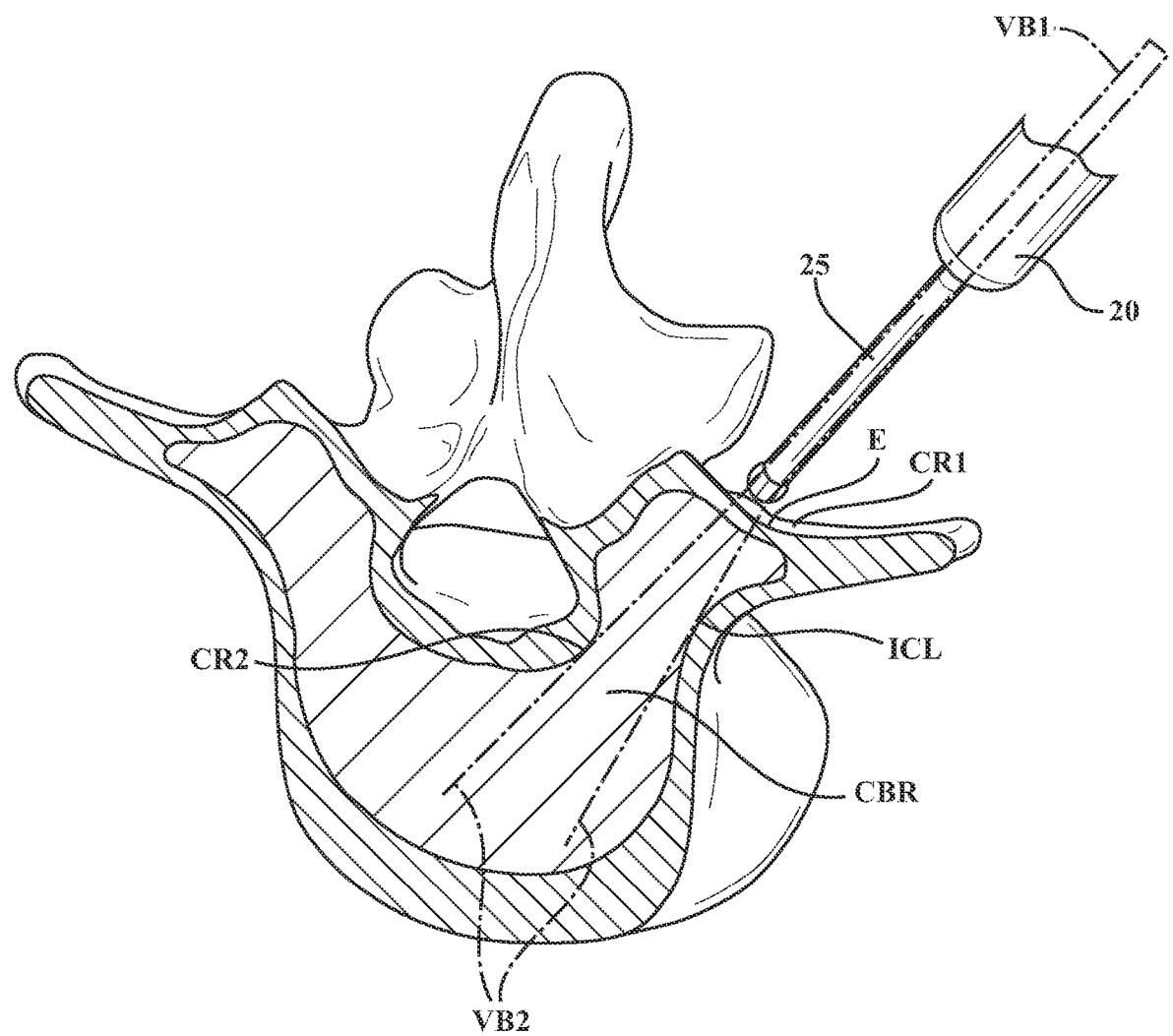
FIG. 8 illustrates first and second virtual boundaries defined relative to the vertebra, wherein the first virtual boundary enables external guidance of the tool to the entry point of the vertebra and the second virtual boundary enables internal guidance and flexibility for cannulation.

To protect damaging the first cortical region (CR1) or causing excessive movement of the vertebra (V) by the robotic manipulator 14, virtual boundaries (VB), for example, as shown in FIG. 5B and FIG. 8, can be associated with the entry point (E) at the first cortical region (CR1). Such virtual boundaries (VB) can constrain lateral and/or axial movement of the cutting axis (CA) relative to the entry point (E). For example, the virtual boundary (VB) can be an hourglass shaped constraint where the narrow waist of the hourglass constraint is positioned at the first cortical region (CR1). Other types of boundary shapes may be utilized, such as lines, cones, etc. The above controls may be performed semi-autonomously or automatically by the system 10. Alternatively, by virtue of feeling vibrational contact between the tool 20 and/or bur 24 and the second cortical region (CR2) an operator can manually change trajectory of the tool 20 and/or bur 24 in the manual mode of operation. The virtual boundaries (VB) can also be associated with the second cortical region (CR2) or any part of the cancellous bone region (CBR).

In another example, the robotic manipulator 14 is configured to adjust a cutting speed of the bur 24 to reduce contact between the tool 20 and/or bur 24 and the second cortical region (CR2). The cutting speed is defined as the amount of revolutions of the bur 24 about the cutting axis (CA) for a period of time (e.g., revolutions/time). In one example, once the sensors 70 detect forces by the second cortical region (CR2), the one or more controllers 30, 60, 62 can change the feed rate of the tool 20 and/or bur 24, i.e., the speed at which the tool 20 and/or bur 24 advances, e.g., along a pathway, over a period of time (e.g., distance of traversal/time). For instance, the feed rate can be 5 mm per second within the cancellous bone region (CBR) until forces are detected from contact with the second cortical region (CR2). At that time, the feed rate can be changed to 0 mm per second, effectively stopping advancement of the tool 20 and/or bur 24 and rending the tool 20 and/or bur 24 incapable of milling cortical bone. The above controls may be performed semi-autonomously or automatically by the system 10. Alternatively, the operator, by virtue of feeling vibrational contact between the tool 20 and/or bur 24 and the second cortical region (CR2) can manually change the feed rate to reduce contact.

In other examples, the one or more controllers 30, 60, 62 can instruct retracting of the tool 20 and/or bur 24 away from the second cortical region (CR2) to reduce forces between the tool 20 and/or bur 24 and the second cortical region (CR2) to avoid breaching the same. For instance, the feed rate can be changed from 0 mm per second to −5 mm per second, advancing the tool 20 and/or bur 24 along the target axis (TA) in a direction exiting the vertebra (V). The above controls may be performed semi-autonomously or automatically by the system 10. Alternatively, the operator, by virtue of feeling vibrational contact between the tool 20 and/or bur 24 and the second cortical region (CR2) can pull the tool 20 and/or bur 24 away from the second cortical region (CR2) in the manual mode of operation.

In yet another example, the one or more controllers 30, 60, 62 can instruct adjusting a cutting parameter of the tool 20 and/or bur 24 to reduce forces between the tool 20 and/or bur 24 and the second cortical region (CR2). For instance, the rotational direction of the bur 24 can be changed to be opposite of the cutting direction, in turn, rendering the bur incapable of effectively cutting cortical tissue, yet allowing milling of the cancellous bone region (CBR) while providing vibrational feedback to the surgeon. In another example, rotation of the bur 24 is stopped. The rotational speed of the bur 24 can also be changed to be lesser than the rotational speed utilized to mill the first cortical region (CR1) or cancellous bone region (CBR). For example, the rotational speed can be 250 rpm for milling bone, but changed to 25 rpm or less, when contact with the second cortical region (CR2) is detected. In other instances, the operator, by virtue of feeling vibrational contact between the tool 20 and/or bur 24 and the second cortical region (CR2) can pull the tool 20 and/or bur 24 away from the second cortical region (CR2) in the manual mode of operation. The above controls may be performed semi-autonomously or automatically by the system 10. Alternatively, the operator, by virtue of feeling vibrational contact between the tool 20 and/or bur 24 and the second cortical region (CR2) can change the rotational speed or direction of the tool 20 and/or bur 24 to reduce contact forces with the second cortical region (CR2). Any of the above techniques may be utilized in combination, simultaneously, or in sequence.

As described, the one or more controllers 30, 60, 62 control the robotic manipulator 14 to cause the tool 20 and/or bur 24 to penetrate the first cortical region (CR1) and enter the cancellous bone region (CBR). In such instances, the one or more sensors 70 are configured to sense forces applied to the tool 20 and/or bur 24 by the first cortical region (CR1) and/or the cancellous bone region (CBR) and the one or more controllers 30, 60, 62 are configured to analyze measurements from the one or more sensors 70 to detect a transition between the first cortical region (CR1) and the cancellous bone region (CBR). These transitions can be detected by storing expected forces for the regions (CR1, CBR) in memory of the one or more controllers 30, 60, 62 and comparing actual force measurements to the same. For instance, the forces applied to the tool 20 and/or bur 24 may be reduced by 50% or less once the tool 20 and/or bur 24 enters the cancellous bone region (CBR) after puncturing the first cortical region (CR1). Throughout the region transitions, the sensors 70 can detect, and the one or more controllers 30, 60, 62 can monitor the force measurements over time. As described, examples of such measurements can be based on torque demand on the tool 20 and/or bur 24 and/or detecting the depth of penetration of the tool 20 and/or bur 24 through any region. Any of the techniques described above, such as adjusting a trajectory of the tool 20 and/or bur 24, reducing a cutting speed of the bur 24, reducing a feed rate of the tool 20 and/or bur 24, reversing a rotational cutting direction of the bur 24, and/or pulling the tool 20 and/or bur 24 away can be applied in response to the one or more controllers 30, 60, 62 detecting region transitions, such as the transition from the first cortical region (CR1) to the cancellous bone region (CBR), or the transition from the cancellous bone region (CBR) to the second cortical region (CR2), and vice-versa.

Figure 7A:
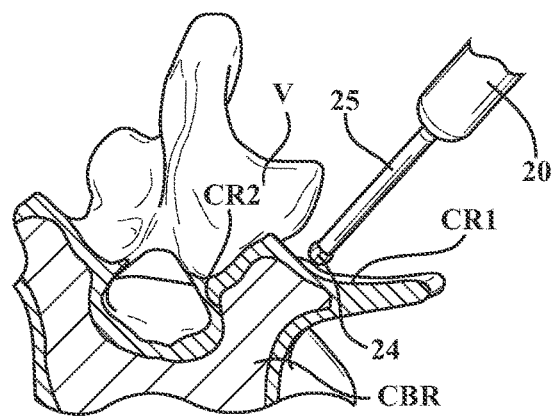
FIGS. 7A-7D illustrate progressive movement of the tool advanced relative to regions of the vertebra for pedicle cannulation, wherein the tool breaches the outer cortical region in a cutting mode (FIG. 7B), displaces cancellous bone in a non-cutting mode (FIGS. 7C-7E) and is controlled to avoid breach of the inner cortical region (FIG. 7F).
Figure 7B:
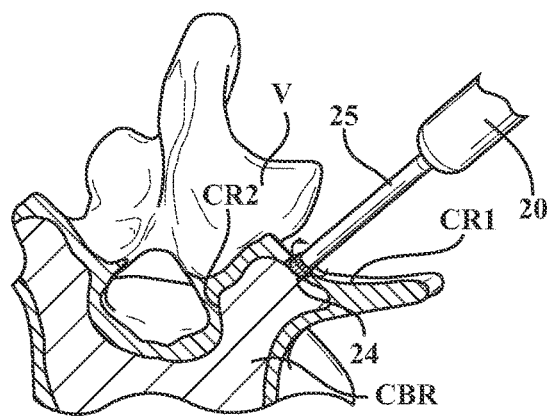

FIGS. 7A-7E illustrate one example of how the cannulation with the tool 20 and/or bur 24 can be executed utilizing a combination of cutting and non-cutting modes. In these examples, a spherical bur 24 is utilized. In FIG. 7A, the one or more controllers 30, 60, 62 facilitate advancement of the tool 20 and/or bur 24 towards the first cortical region (CR1). In FIG. 7B, the one or more controllers 30, 60, 62 control the tool 20 and/or bur 24 in a cutting mode to penetrate the first cortical region (CR1). In the cutting mode, the tool 20 and/or bur 24 is actively actuated to remove material from the first cortical region (CR1). For example, in the cutting mode, the bur can be rotated at a high rate of cutting speed, e.g., 10,000-11,000 RPM.

Figure 7C:
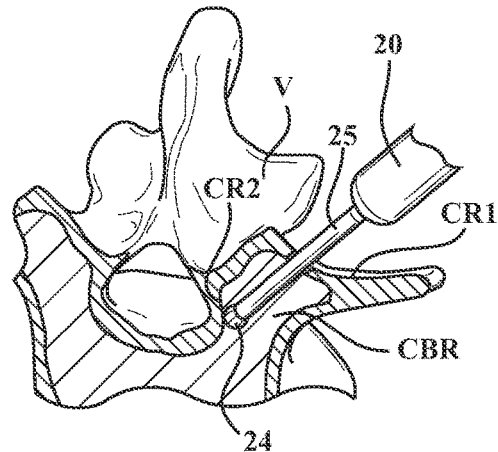

In FIG. 7C, in response to detecting a transition from the first cortical region (CR1) to the cancellous bone region (CBR), the one or more controllers 30, 60, 62 are configured to switch operation of the tool 20 and/or bur 24 to a non-cutting mode wherein the tool 20 and/or bur 24 is not actuated and passively interacts with the cancellous bone region (CBR) based on advancement of the tool 20 and/or bur 24 through the cancellous bone region (CBR) by the robotic manipulator 14. In other words, the bur is not rotated, and operates as a passive probe that penetrates and displaces cancellous bone region (CBR) by virtue of its advancement by the manipulator 14. In another example, non-cutting mode may comprise any operation of the tool 20 and/or bur 24 whereby the tool may be actively energized, but ineffective as a milling tool for removing tissue, as compared with the cutting mode. For example, the bur 24 can rotate at a low cutting speed and/or in reverse cutting direction.

Figure 7D:
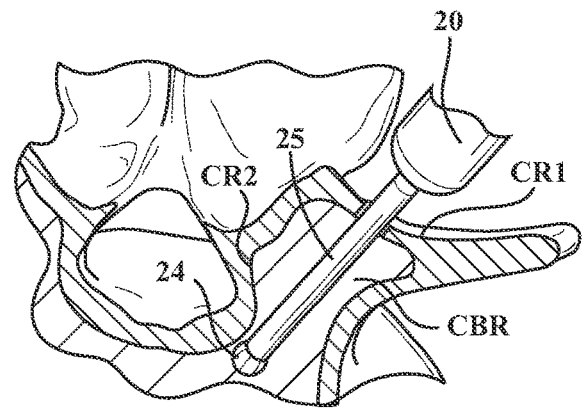

In FIG. 7D, the one or more controllers 30, 60, 62 continue to instruct advancement of the tool 20 and/or bur 24 in the non-cutting mode within the cancellous bone region (CBR) while the one or more sensors 70 detect forces applied to the tool 20 and/or bur 24.

Figure 7E:
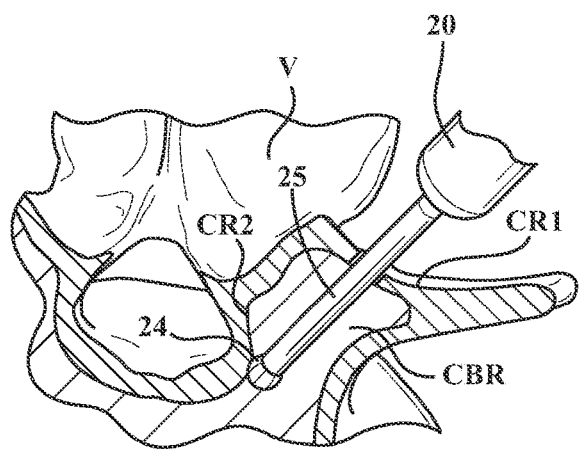

Eventually, in FIG. 7E, the tool 20 and/or bur 24 is advanced in the non-cutting mode to the point where it reaches the second cortical region (CR2). In other words, the one or more controllers 30, 60, 62 can detect another transition, i.e., from the cancellous bone region (CBR) to the second cortical region (CR2). In response to detecting the transition to the second cortical region (CR2), or forces applied to the surgical tool by the second cortical region (CR2), the one or more controllers 30, 60, 62 control the robotic manipulator 14 and/or tool 20 to reduce forces applied to the tool 20 and/or bur 24 by the second cortical region (CR2) by utilizing any of the techniques described above, such as adjusting a trajectory of the tool 20 and/or bur 24, reducing a feed rate of the tool 20 and/or bur 24, and/or pulling the tool 20 and/or bur 24 away from the second cortical region (CR2).

Figure 7F:
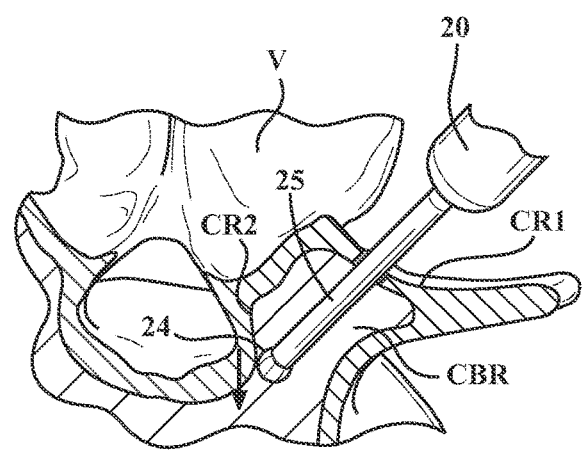

In one example, as shown in FIG. 7F, during the non-cutting mode, the tool 20 and/or bur 24 is advanced to contact the second cortical region (CR2). During advancement, the spherical geometry of the bur causes a deflection or intentional skiving of the bur along the second cortical region (CR2) until the bur eventually slips off the second cortical region (CR2) (as shown by the arrow). In turn, this technique provides cannulation for the pedicle screw while avoiding breach of the second cortical region (CR2).

Switching from cutting mode to the non-cutting mode in response to detecting region transition may occur immediately or after a predetermined time or distance/displacement. For example, the switch to non-cutting mode may occur after a displacement of the bur 24 by minimum of 5 mm past the entry point (E) into the cancellous bone region (CBR).

Furthermore, the non-cutting mode may also provide advancement of the tool 20 and/or bur 24 according to various different methods. In one example, advancement is continuous and constant over a distance or time. Advancement may also be variable in velocity. In other examples, the robotic manipulator 14 controls the tool 20 and/or bur 24 in a "tap and advance" motion, mimicking a jackhammer motion, whereby the tool 20 and/or bur 24 is advanced a by a tapping distance of 0.1-3 mm, followed by a pause, or retraction. This technique may be beneficial because of the tolerances involved with motion of the tool 20 and/or bur 24 in the cancellous bone region (CBR). Thereafter, this tapping is repeated until advancement is stopped by any suitable event, such as detection of the second cortical wall (CR2) or the user stopping advancement in the manual mode. The one or more sensors 70 can sense forces on the tool 20 and/or bur 24 for tapping motions and the one or more controllers 30, 60, 62 can make dynamic adjustments to the tool 20 and/or bur 24 operation or trajectory to reduce forces experienced during cannulation.

Any combination of the aforementioned control techniques can be utilized in further combination with the cutting and non-cutting mode as well as with control responsive to detecting transitions between regions of the vertebra. Furthermore, the one or more controllers 30, 60, 62 are further configured to control the robotic manipulator 14 in any combination of the manual mode or semi-autonomous mode to enable control of the tool 20 and/or bur 24 to penetrate any region of the vertebra (V) described herein. Furthermore, the one or more controllers 30, 60, 62 are configured to operate the tool 20 and/or bur 24 in the cutting mode or non-cutting mode simultaneously while enabling control of the robotic manipulator 14 in the manual or semi-autonomous modes.

For any of the examples above, the cannulation provided by the tool 20 and/or bur 24 and control of the tool 20 and/or bur 24 to avoid breach of the second cortical wall (CR2) can be facilitated using one or more virtual boundaries (VB) constraining movement of the tool 20 and/or bur 24 with respect to the vertebra (V). The virtual boundary (VB) can be defined with respect to a surgical plan associated with the anatomical model of the vertebra. By registering the surgical plan to the vertebra, and by tracking movement of the tool 20 and/or bur 24 and the vertebra using any modality of the navigation system 32, the one or more controllers 30, 60, 62 can constrain movement of the tool 20 and/or bur 24 by the virtual boundary (VB). The virtual boundary (VB) may be defined external to and/or internal to the vertebra (V). Externally, the virtual boundary (VB) may be defined to constraint movement of the tool 20 and/or bur 24 towards the entry point (E), which can also be registered to the surgical plan. The virtual boundary (VB) can be a line haptic, providing an axis or line along which the tool 20 and/or bur 24 traverses to reach the entry point (E). Alternatively or additionally, the virtual boundary (VB) can be a cone shape, having the vertex at or near the entry point (E) and the base above the vertebra. Other virtual boundary geometries for guiding the tool 20 and/or bur 24 to the entry point (E) are envisioned. Internally, the virtual boundary can be an extension of the external virtual boundary or a separate virtual boundary. The internal virtual boundary can similar be a line, cone, or the like. The virtual boundaries may define different stiffness or damping parameters, changing the extent to which the tool 20 and/or bur 24 is constrained to or by the virtual boundary (VB).

In one example, as shown in FIG. 8, the one or more controllers 30, 60, 62 are configured to define a first virtual boundary (VB1) constraining movement of the tool 20 and/or bur 24 according to a first lateral compliance, and to define a second virtual boundary (VB2) constraining movement of the tool 20 and/or bur 24 according to a second lateral compliance. The second virtual boundary (VB2) provides greater lateral compliance for the cutting bur 24 than the first virtual boundary (VB1). In other words, the tool 20 and/or bur 24 is able to move more freely relative to the second virtual boundary (VB2) as compared to the first virtual boundary (VB1). The lateral compliance may be realized by stiffness, spring, or damping constraint parameters. Reactive forces may be implemented to prevent the tool 20 and/or bur from exceeding the virtual boundaries (VB1, VB2). Examples of constraints that me be utilized in any of the techniques described herein can be like that described in U.S. patent application Ser. No. 16/584,436, filed Sep. 26, 2019, and entitled "Surgical System and Method Utilizing Impulse Modeling For Controlling An Instrument". The first virtual boundary (VB1) may be external to the vertebra and may be the line haptic for guiding the tool 20 and/or bur 24 to the entry point (E), wherein the tool 20 and/or bur 24 is rigidly constrained to the line haptic. The one or more controllers 30, 60, 62 control the tool 20 and/or bur 24 in the cutting mode by activating the first virtual boundary (VB1) to constrain the tool 20 and/or bur 24 according to the first stiffness parameter to penetrate the first cortical region (CR1) for penetrating the same.

To facilitate internal milling for cannulation, the one or more controllers 30, 60, 62 control the tool 20 and/or bur 24 in the non-cutting mode by activating the second virtual boundary (VB2) to constrain the tool 20 and/or bur 24 according to the second stiffness parameter to advance the tool 20 and/or bur 24 through the cancellous bone region (CBR) by the robotic manipulator 14. As described above, avoiding breach of one or more second cortical regions (CR2) is desired. To facilitate breach avoidance using this technique, the one or more controllers 30, 60, 62 further control the robotic manipulator 14 and/or tool 20 and/or bur 24 to reduce forces applied to the tool 20 and/or bur 24 by the second cortical region (CR2) by further being configured to deflect the tool 20 and/or bur 24 away from the second cortical region (CR2) due to the second stiffness parameter of the second virtual boundary (VB). In other words, since the second virtual boundary (VB) has more tolerance in movement of the tool 20 and/or bur 24, this tolerance can be utilized to maneuver the tool 20 and/or bur 24 out of contact with the second cortical region (CR2). This second virtual boundary may be, for example, a cone having the apex at the entry point (E), and the base of the cone within the cancellous bone region (CBR). Edges of the second virtual boundary (VB2) can be positioned directly near the second cortical regions (CR2) as shown in FIG. 8. The radius of the bur can be accounted for in such positioning. Clearances of the second virtual boundary (VB2) provide the ability to bias the tool 20 and/or bur 24 in order to detect the second cortical wall (CR2) and/or to follow a more anatomically correct trajectory. This maneuvering can be performed in the manual mode of operation. It is not required that the first virtual boundary (VB1) be stiffer than the second virtual boundary (VB2) to facilitate this maneuver. Rather, the stiffness parameter of the second virtual boundary (VB2) can be loose or tolerant enough to maneuvering of the tool 20 and/or bur 24 away from the second cortical region (CR2) while disposed within the cortical bone region (CBR).

In other examples, applicable to any aspect described herein related to cannulation, the one or more sensors 70 can be configured to sense forces applied to the cutting bur 24 by the cancellous bone region (CBR). These forces can be axial, i.e., in a direction along the cutting axis (CA) and/or lateral in a direction transverse to the cutting axis (CA). During advancement of the cutting bur 24 through the cancellous bone region (CBR), the one or more controllers 30 compare the sensed forces to a predetermined force threshold. This force threshold is defined to prevent displacement of the bone structure from force applied by the cutting bur 24. In other words, this technique has the advantage to control cannulation with the bur 24 such that the bone structure is not undesirably displaced by the bur in an axial and/or lateral direction. This enables greater accuracy for cannulation as compared with past manual cannulation techniques. The force data and threshold can be based on prior clinical data and force measurements, the system may store in a non-transitory computer readable medium, data, a matrix, or look-up table relating force measurements to anticipated movement of the bone structure. This data can be based on parameters such as, but not limited to: (1) geometry of bur, including bur size, thickness, shape (2) type of bone structure, (3) density or quality of cancellous bone region, (4) feed rate of the bur, (5) cutting speed of the bur, (6) kinematic information regarding the manipulator, (7) patient specific information, (8) statistical patient information, (9) surgical plan, including implant size, and (10) surgeon preference information. The force threshold can be an upper limit, lower limit, or an acceptable range of values. Based on the sensed forces, the one or more controllers 30 can regulate, modulate, or otherwise dynamically modify operation parameters of the tool 20, such as the feed rate at which the bur 24 passes through the cancellous bone region (CBR). The one or more controllers 30, based on the sensed forces, may also adjust a trajectory of the cutting axis (CA) to mitigate force.

The above force-sensing technique can be utilized while the bur 24 is utilized for cannulation in the cutting mode or non-cutting mode. However, when the bur 24 is actively cutting during cannulation in the cutting mode, it may be desirable to monitor forces to not only for avoiding displacement of the bone structure, but also to ensure the bur 24 advances at a feed rate, pressure and/or force (N/m) desired or required by the system 10, e.g., manipulator, to enable proper cannulation based on bur 24 operation while at the same time avoiding trauma or excessive cutting speeds within the cancellous bone region (CBR). In turn, based on the sensed forces, the one or more controllers 40 can adjust one or more of a rotational cutting speed of the cutting bur 24 and the feed rate of the surgical tool 20 to maintain advancement of the cutting bur 24 through the cancellous bone region (CBR). The one or more controllers 30, based on the sensed forces, may also adjust a trajectory of the cutting axis (CA) to mitigate force. Again, these techniques can be employed for axial forces, lateral forces, or a combination of lateral and axial forces. In some instances, the cutting speed inside the cancellous bone region (CBR) can be from 5-500 RPM.

Once again, any combination of the aforementioned control techniques can be utilized in further combination with the cutting and non-cutting mode as well as with control responsive to detecting transitions between regions of the vertebra. Furthermore, the one or more controllers 30, 60, 62 are further configured to control the robotic manipulator 14 in any combination of the manual mode or semi-autonomous mode to enable control of the tool 20 and/or bur 24 to penetrate any region of the vertebra (V) described herein. Furthermore, the one or more controllers 30, 60, 62 are configured to operate the tool 20 and/or bur 24 in the cutting mode or non-cutting mode simultaneously while enabling control of the robotic manipulator 14 in the manual or semi-autonomous modes.

B. Robotic Techniques for Avoiding Skiving at Entry Point

The techniques above have been described in reference to reducing forces between the tool 20 and/or bur 24 and the second cortical region (CR2) for avoiding breach of the same. However, similar techniques can be applied in regards to contact between the tool 20 and/or bur 24 and the first cortical region (CR1).

As described, the one or more controllers 30, 60, 62 can control the manipulator 14 to control the tool 20 and/or bur 24 to manipulate the first cortical region (CR1), e.g., for creating an entry point (E) into the vertebra for pedicle screw insertion (as shown in FIG. 3C for example). The one or more sensors 70 can also be configured to sense forces applied to the tool 20 and/or bur 24 by the first cortical region (CR1) during penetration. To avoiding the tool 20 and/or bur 24 skiving with respect to the first cortical region (CR1), the one or more controllers 30, 60, 62 control the robotic manipulator 14 and/or tool 20 and/or bur 24 to reduce forces applied to the tool 20 and/or bur 24 by the first cortical region (CR1) by performing any of the techniques described above, such as adjusting a trajectory of the tool 20 and/or bur 24, reducing a cutting speed of the tool 20 and/or bur 24, reducing a feed rate of the tool 20 and/or bur 24, reversing a rotational cutting direction of the tool 20 and/or bur 24, and/or pulling the tool 20 and/or bur 24 away from the first cortical region (CR1).

To facilitate avoidance of skiving, any combination of the aforementioned control techniques can be utilized in further combination with the cutting and non-cutting mode as well as with control responsive to detecting transitions between regions of the vertebra. Furthermore, the one or more controllers 30, 60, 62 are further configured to control the robotic manipulator 14 in any combination of the manual mode or semi-autonomous mode to enable control of the tool 20 and/or bur 24 to penetrate the first cortical region (CR1) to create the entry point (E). The further facilitate avoidance of skiving, the one or more controllers 30, 60, 62 are configured to operate the tool 20 and/or bur 24 in the cutting mode or non-cutting mode simultaneously while enabling control of the robotic manipulator 14 in the manual or semi-autonomous modes. For example, the mode can be switched to from cutting mode to non-cutting mode when forces indicative of skiving are detected.

To avoid skiving, aggressiveness of the bur 24 cutting speed can be modulated or controlled as the cutting bur 24 approaches the first cortical region (CR1) to create the entry point (E). In one example, the bur 24 is rotated at high speed, e.g., 10,000-11,000 RPM to create a spot facing feature (or notch) into the first cortical region (CR1) at the entry point (E). In turn, this creates a bur-shaped carving of the bone to guide the bur 24 during a second pass to avoid skiving. For example, on the second pass, the bur 24 can return to the spot facing feature after slightly retracting away from the spot facing feature. Alternatively, on the second pass, the bur 24 may be reactivated and being disabled while in the same position it was immediately after spot facing. One the second pass, the bur 24 may once again but rotated at a cutting speed (e.g., high cutting speed) to penetrate the first cortical region (CR1) at the region of the spot facing feature. The controlled feed-rate techniques described herein may also be utilized to manage the feed rate of the bur 24 relative to the spot facing feature to further enhance skiving avoidance capabilities.

The above techniques reduce potential surgeon errors by utilizing the robotic system to detect and avoid skiving and by further providing robotically controlled ability to bias the entry point (E) for the tool 20 and/or bur 24 by controlling the tool 20 and/or bur 24 in a restorative manner against the skiving direction.

C. Robotic Techniques for Landmark Detection to Determine Entry Point

In addition to the techniques described herein focusing on pedicle cannulation while avoiding breach of cortical bone as well as skiving, the forces applied to the tool 20 and/or bur 24 can be sensed for other purposes, such as detecting landmarks on vertebra for surgical planning.

Figure 9:
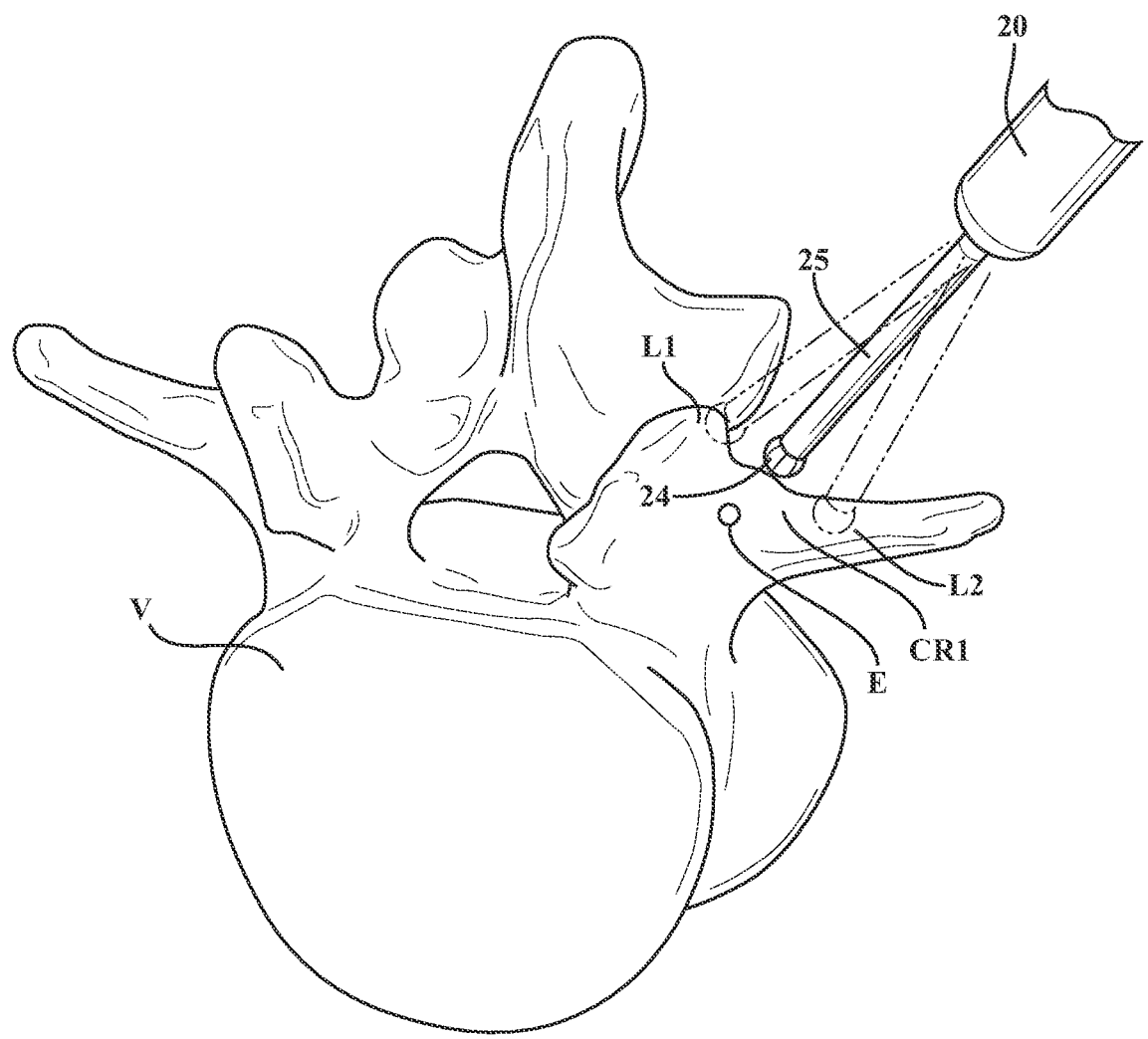
FIG. 9 illustrates control of the tool relative to the outer cortical region of the vertebra to facilitate landmark detection with the tool for confirmation of the entry point for pedicle cannulation.

With reference to FIG. 9, the vertebra (V) comprises actual anatomical landmarks (L1, L2) that can be referenced by the system to provide guidance for the surgeon in locating the proper entry point (E) for pedicle cannulation. Such actual anatomical landmarks can be sloped or slanted surfaces of bone, such as the facet joint (shown at L1) and the transverse process (shown at L2) in the pedicle region of the vertebra (V). These actual landmarks (L1, L2) serve as detectable topographies confirming the entry point (E). Of course, other types of landmarks are contemplated other than those described for the vertebra, and landmarks may be different for depending on the bone (e.g., femur, skull, ribs, etc.).

The navigation system 32 described herein is configured to track an actual position of the tool 20 and/or bur 24 relative to the vertebra (V). The one or more controllers 30, 60, 62 store a virtual model of the first cortical region (CR1) comprising data identifying the predetermined anatomical landmarks of the first cortical region (CR1), such as the facet joint and transverse process. The virtual model of the first cortical region (CR1) can derived from pre-operative imaging data of the vertebra, using any imaging modality, such as CT imaging. The virtual model may also be created by morphing a statistical model of the vertebra. Alternatively, the virtual model can be generated intraoperatively, using techniques such as point-cloud construction using the pointer P or the tool 20 and/or bur 24, ultrasound imaging, or X-ray or fluoroscopy imaging.

In some instances, the navigation system 32 can directly track the vertebra (V), however, this is not required. The one or more controllers 30, 60, 62 control the robotic manipulator 14 to cause the tool 20 and/or bur 24 to interact with the actual anatomical landmarks of the first cortical region (CR1). The one or more sensors 70 are configured to sense actual forces applied to the tool 20 and/or bur 24 by the actual anatomical landmarks. This manipulation can be in the non-cutting mode, wherein the tool 20 and/or bur 24 is not actuated, but is utilized to "feel" the landmarks. Furthermore, motion of the tool 20 and/or bur 24 can be executed in the manual or semi-autonomous modes. In the manual mode, the operator, by virtue of feeling vibrational contact between the tool 20 and/or bur 24 and the actual anatomical landmarks, can manually confirm positioning of the entry point (E).

Additionally, or alternatively, the one or more controllers 30, 60, 62 store data correlating expected force measurements from the one or more sensors 70 and expected position of the tool 20 and/or bur 24 to the predetermined anatomical landmarks of the first cortical region (CR1). This data can be stored in a look-up table or force/position matrix, and may be correlated to the geometry of the virtual model. The one or more controllers 30, 60, 62 receive measurements from the one or more sensors 70 resulting from actual forces applied to the tool 20 and/or bur 24 by the actual anatomical landmark(s). Meanwhile, the one or more controllers 30, 60, 62 receive actual position of the tool 20 and/or bur 24 from the navigation system 32 during this manipulation. The one or more controllers 30, 60, 62 compare the actual force measurements from the one or more sensors 70 and the actual position of the tool 20 and/or bur 24 from the navigation system 32 with the expected force measurements and expected position of the tool 20 and/or bur 24. Through this comparison, the one or more controllers 30, 60, 62 can associate the actual anatomical landmark(s) manipulated by the tool 20 and/or bur 24 with one of the predetermined anatomical landmarks of the first cortical region (CR1).

Analysis of the actual position of the tool 20 and/or bur 24 can include tracking parameters other than position. For example, the one or more controllers 30, 60, 62 can determine a displacement or depth of the tool center point TCP of the tool 20 and/or bur 24 relative to one or more reference points. These reference points may be defined relative to the vertebra (V) or may be at a control position known to the system.

Confirmation of entry point (E) can be performed by the system generating a notification or visual confirmation with the navigation system 32. Once confirmation is received, the entry point (E) can either be registered to the virtual model for updating of the surgical plan or the surgeon can manually execute milling of the entry point (E) based on knowledge acquired during the robotically-assisted confirmation process.

Furthermore, motion of the tool 20 and/or bur 24 relative to these landmarks may be constrained by a virtual boundary (VB) associated with the first cortical region (CR1) to avoid excessive motion of the tool 20 and/or bur 24 relative to other sensitive spinal structures outside of the region of interest.

To further facilitate entry point (E) confirmation, any combination of the aforementioned control techniques can be utilized in further combination with the cutting and non-cutting mode. Furthermore, the one or more controllers 30, 60, 62 are further configured to control the robotic manipulator 14 in any combination of the manual mode or semi-autonomous mode to enable confirmation of the entry point (E).

The above techniques reduce potential surgeon errors by providing robotic and navigation guidance to assist the surgeon to feel the "docking" of the tool 20 and/or bur 24 on the entry point (E) of the pedicle.

D. Robotic Hardware and Control Techniques for Managing Tool Operation for Cortical Bone Penetration and Cancellous Bone Cannulation With reference to FIGS. 10-11, described herein are robotic hardware and control techniques for managing tool operation for cannulation. As will be understood below, such tool operations include feed rate, rotational speed, modes of operation, and the like.

The feed rate of the tool 20 and/or bur 24 is the rate at which the tool 20 and/or bur 24 advances along a path or trajectory. The feed rate can be defined by the path generator 69 and executed by the manipulator controller 60. However, any of the controllers 30, 60, 62 can be utilized in combination.

The hardware and techniques described herein provide a technical solution of managing user control of the feed rate, wherein the user may desire to advance the tool 20 and/or bur 24 at a high feed rate to expedite the surgical procedure. Such haste and mismanagement of the feed rate can cause joint loading or flexing beyond desirable positions. Such flexing may trigger a runaway feedback loop wherein the system controls the robotic manipulator 14 to recover position of the TCP of the tool 20 and/or bur 24 position on the tool path registered to the vertebra. However, the position on the tool path is pushed out of position due to the flexing of the vertebra caused by excessive feed rate. In turn, the system may move the tool 20 and/or bur 24, and in doing so, cause further flexing of the vertebra. The system may continually attempt to reach an unreachable position with the TCP of the tool 20 and/or bur 24. Additionally, managing user control of the feed rate is notable to avoid skiving, a condition prevalent at the entry point (E) of the vertebra.

As described, the tool 20 is or forms part of the end effector 22. The robotic manipulator 14 is configured to support and move the end effector 22 relative to the vertebra to manipulate the vertebra (V). The tool 20 and/or end effector 22 can be like that shown in FIGS. 10-11, or like that described in U.S. Patent Application Publication No. 2014/0276949, filed on Mar. 15, 2014, entitled, "End Effector of a Surgical Robotic Manipulator," or like that described in U.S. patent application Ser. No. 16/184,376, filed Nov. 8, 2018, entitled "Robotic Spine Surgery System And Methods," the entire contents both being hereby incorporated by reference.

As shown, the end effector 22 comprises a control interface 80 integrated with the end effector 22 and being configured to enable manual control of a feed rate of the tool 20 and/or bur 24. As shown, the control interface 80 is integrated such that the operator can directly grasp the control interface 80 by hand while operating the end effector 22. This configuration also provides the advantage of providing the operator with a vibrational feel of the tool 20 and/or bur 24 operation relative to the vertebra (V). Simultaneously, it is possible that the operator can apply external forces to the end effector 22 by hand, causing the force/torque sensor coupled between the end effector 22 and the arm of robotic manipulator, to detect the external forces for initiating a transition from semi-autonomous to the manual mode or for allowing the surgeon to manually reorient the cutting axis (CA) of the tool 20 and/or bur 24. The one or more controllers 30, 60, 62 control the robotic manipulator 14 to align the tool 20 and/or bur 24 to the target axis (TA) associated with the vertebra of interest. The one or more controllers 30, 60, 62 to manage the feed rate of the tool 20 and/or bur 24 with respect to the target axis (TA) in response to user interaction with the control interface 80. Management of the feed rate relative to the target axis (TA) may during the approach of the tool 20 and/or bur 24 to the target axis (TA) and/or during motion of the tool 20 and/or bur 24 along the target axis (TA).

Furthermore, the feed rate can be predefined by the one or more controllers 30, 60, 62 depending on conditions such as surgical plan, type of surgical action or step, type of tool, type of end effector, type of control mode, tracked position of the tool, tracked position of the vertebra, detecting bone region transitions, detection of the inner cortical wall, operator preference, or any combination thereof. Alternatively, there may be instances, such as those described below, wherein the operator manually controls the feed rate using the control interface 80.

As shown, the control interface 80 has a joystick type configuration that may be static or moveable. The control interface 80 comprises various tactile interfaces for various controls. These tactile interfaces can include a trigger 82, and one or more buttons 84. In one example, the trigger 82 is configured to signal the one or more controllers 30, 60, 62 to execute activation of the tool 20 and/or bur 24 for milling tissue, e.g., in the cutting mode. The one or more buttons 84 are configured to signal the one or more controllers 30, 60, 62 to control functions of feed rate control, such as starting or stopping of the tool 20 and/or bur 24 movement according to the defined feed rate, requesting confirmation from the user before implementing feed rate movement, and/or changing direction of the tool along the tool path, e.g., according to the defined feed rate. The one or more buttons 82 can be depressed simultaneously with the trigger 82 for executing any of the aforementioned features at the same time.

The joystick configuration shown, including the trigger 82 and button 84 is only one example way of implementing this hardware. In other examples, the trigger 82 and button 84 may be implemented on the end effector 22 body, without a separate joystick. The control interface 80 can also be integrated into or coupled to grasping portion of the end effector 22, which is a portion of the end effector 22 designed to enable the operator to hold the end effector 22 for applying external forces to the same for facilitating control in the manual mode of operation. Furthermore, there may be other means for registering user intention besides the trigger and button. For instance, any type of user input device may be utilized, such as voice control, gesture control, or the like. Also, the tactile interfaces need not be mechanical buttons or triggers, but may be capacitive or heat touch sensors, or the like. Additionally, there may be instances where the control interface 80 is separate from the end effector 22. For instance, the control interface 80 may be a pendant or hand-held control that is wired or wirelessly connected to the one or more controllers 30, 60, 62.

In conjunction with feed rate control described herein, any combination of the aforementioned control techniques from the prior sections can be utilized. For example, the one or more controllers 30, 60, 62 can control the robotic manipulator 14 in the semi-autonomous mode, and may do so simultaneously in the cutting or non-cutting modes.

Figure 10A:
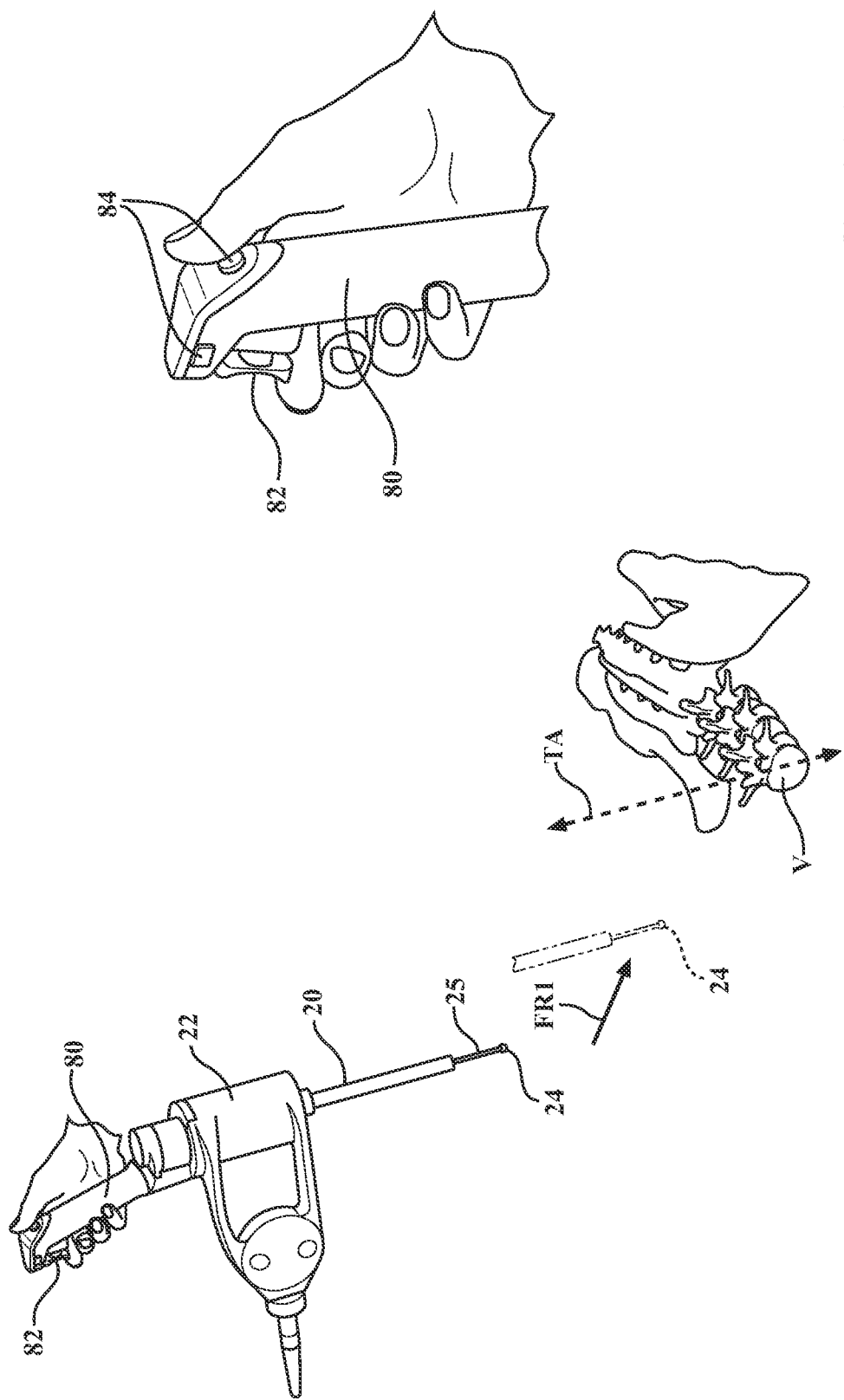
FIGS. 10A-10C illustrate progressive robotically controlled movement and feed rate control of the tool towards a target axis associated with the vertebra utilizing a control interface coupled to the end effector.
Figure 10B:
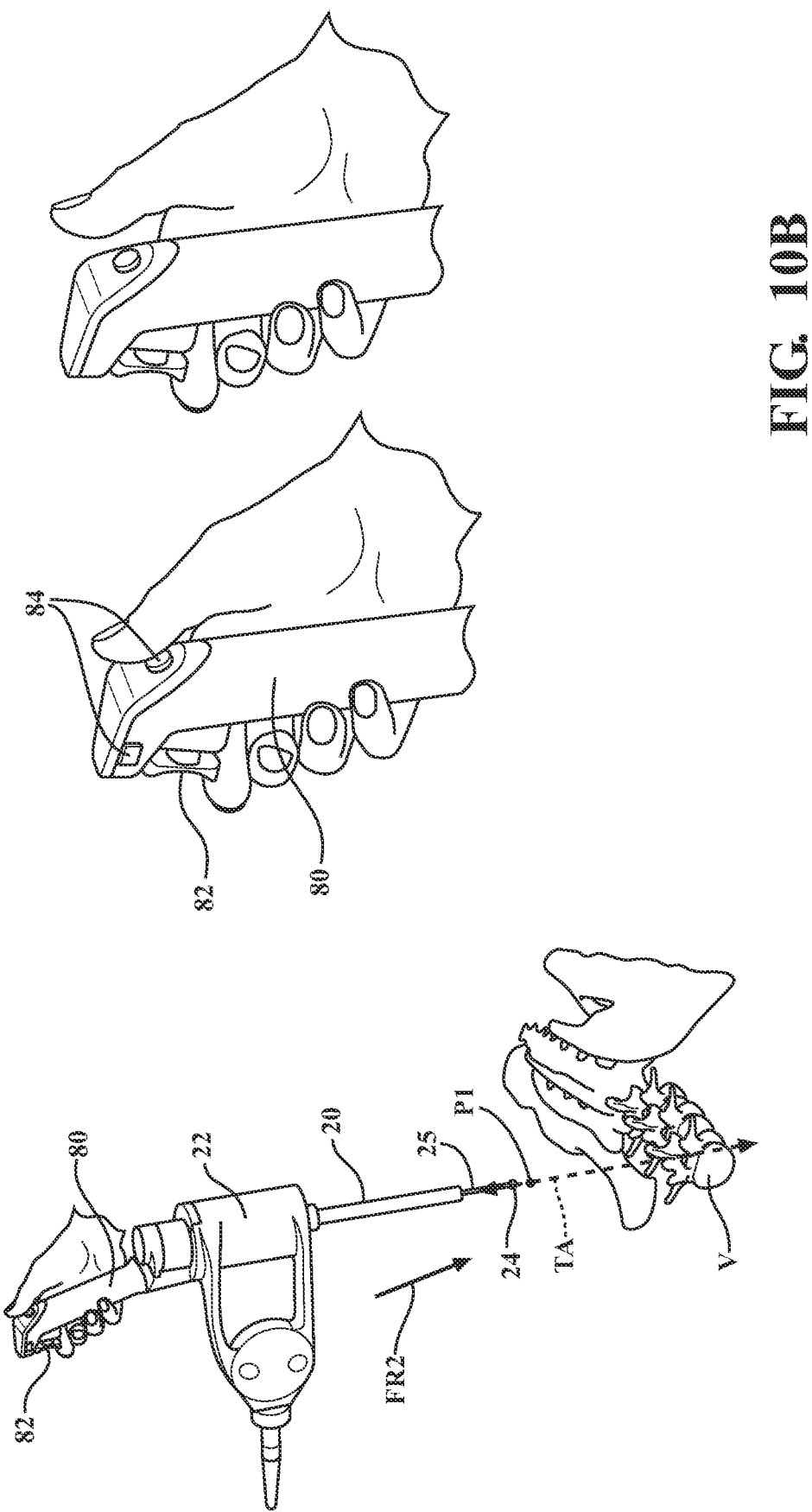
Figure 10C:
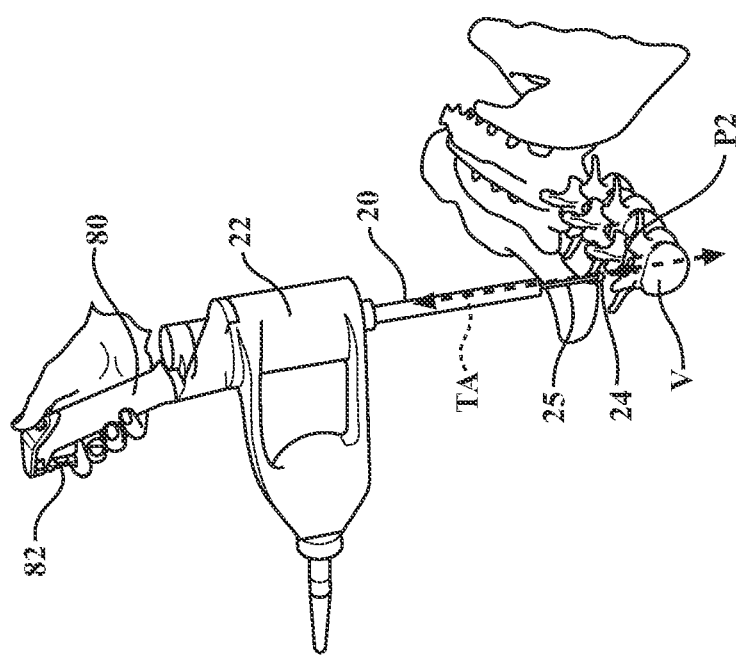

With reference to FIGS. 10A-10C, techniques are described for using the control interface 80 in conjunction with the system for guiding the cutting axis (CA) of the tool 20 and/or bur 24 to the target axis (TA). As shown in FIG. 10A, the cutting axis (CA) of the tool 20 and/or bur 24 is initially positioned away from and off the target axis (TA). To manage the feed rate of the tool 20 and/or bur 24 towards the target axis (TA), the one or more controllers 30, 60, 62 can designate a first feed rate (FR1) for moving the tool in the direction relatively shown by the arrow. Upon depressing the button 84, the robotic manipulator 14 advances the tool 20 and/or bur 24 towards the target axis (TA) in the semi-autonomous mode. Such movement is according to the first feed rate (FR1), which can be defined by the one or more controllers 30, 60, 62 or by the operator. In one example, this feed rate is 30 mm per second. However, this feed rate can be different than the example provided. The first feed rate (FR1) may be higher than other feed rates utilized during approach or cannulation because the tool 20 and/or bur 24 is positioned relatively distant from the vertebra (V).

For any of the examples described herein, the feed rate can be defined by the operator in various manners. In one example, the feed rate may be defined by the operator by interaction with the control interface 80 or more specifically, any of the buttons 84. For instance, force or pressure applied to a button or displacement of a button may be proportional to changes in feed rate. The buttons 84 can include indicia, such as "increase" or "decrease" identifying one or more buttons that can be pressed to increase or decrease the feed rate. In yet another example, the control interface 80 can be configured with the ability to move about different degrees of freedom to provide the user the ability to select the feed rate, or perform other controls, by moving the control interface 80 in certain directions. The control interface 80 can comprise a PCB mounted thumb stick or transducer than can translate physical motion into control signals. For example, the control interface 80 could be tilted forward to increase the feed rate, tilted backwards to reduce the feed rate, and pressed down to make a selection of feed rate. In other examples, the feed rate can be selected using the input devices of the navigation system 32. Other examples are contemplated for selecting the feed rate.

Regardless of how the feed rate is defined, it is possible for certain advancements of the tool 20 and/or bur 24 relative to the vertebra (V), that the one or more controllers 30, 60, 62 designate certain feed rates to prevent the user from using excessive feed rates potentially causing the aforementioned errors. As will be described below, the feed rate for certain other advancements of the tool 20 and/or bur 24 can be delegated to the user instead of being designated by the system.

Any changes in the feed rate, whether defined by the user or predefined by the one or more controllers 30, 60, 62, can be displayed on the displays of the navigation system 32. Any suitable display graphic may be utilized, such as a sliding scale for the chosen feed rate, or the like. In some examples, the end effector 22 and/or the control interface 80 can have a display unit for displaying the feed rate chosen. Other examples are contemplated for displaying the chosen feed rate.

In FIG. 10B, the tool 20 and/or bur 24 has advanced according to the first feed rate (FR1) to move from the initial position to reach a first position P1 that is on, or nearer to the target axis (TA) and/or vertebra (V). This first position P1 may be predefined by the one or more controllers 30, 60, 62. Alternatively, this first position P1 may be grossly identified by the surgeon based on experience. The navigation system 32 can be utilized to detect the first position P1 by tracking the TCP of to the tool 20 and/or bur 24. The end effector 22 movement may be halted at the first position P1 by the one or more controllers 30, 60, 62 or may be manually halted by the user control of the interface 80, e.g., releasing the button 84.

If halted by the one or more controllers 30, 60, 62, the system may request the user to perform a confirmation process as a check in view of the increasing proximity of the tool 20 and/or bur 24 to the vertebra (V). In one example, as shown, the user releases the button 84 and presses it once more to confirm that further approach is desired. This confirmation may take various forms other than that shown. For example, the confirmation may be visual, audible, and/or haptic, and may not involve interaction with the control interface 80. For instance, the navigation system 32 may generate a notification requesting user confirmation, which can be confirmed using input devices of the navigation system 32.

Once confirmation is received, the user once again depresses the button 84, and the robotic manipulator 14 advances the tool 20 and/or bur 24 closer to, or along, the target axis (TA) in the semi-autonomous mode. Such movement is according to a designated second feed rate (FR2) as shown in FIG. 10B, which can be defined by the one or more controllers 30, 60, 62 or by the operator. In one example, this second feed rate (FR2) is slower than the first feed rate (FR1), and can be 20 mm per second. The second feed rate (FR2) may be slower than the first feed rate (FR1) because the tool 20 and/or bur 24 is positioned relatively closer to the vertebra (V).

In FIG. 10C, the tool 20 and/or bur 24 has advanced according to the designated second feed rate (FR2) from the first position P1 to a second position P2. The second position P2, in this example, is on the target axis (TA) and closer to the vertebra (V) as compared with the first position P1. Similarly, this second position P2 may be predefined by the one or more controllers 30, 60, 62. Alternatively, this second position P2 may be grossly identified by the surgeon based on experience. In one example, this second position P2 is a predetermined distance from the entry point (E) of the vertebra (V). For instance, the second position P2 may be displaced 5 mm above the entry point (E). Other distances are contemplated. The navigation system 32 can be utilized to detect this second position P2 by tracking the TCP of to the tool 20 and/or bur 24. The end effector 22 movement may once again be halted at this second position P2 by the one or more controllers 30, 60, 62 or may be manually halted by the user control of the interface 80.

FIGS. 11A-11F illustrate robotically controlled movement of the tool 20 and/or bur 24 along the target axis (TA) for pedicle cannulation, with advanced tool operation being facilitated by the control interface 80.

Figure 11A:
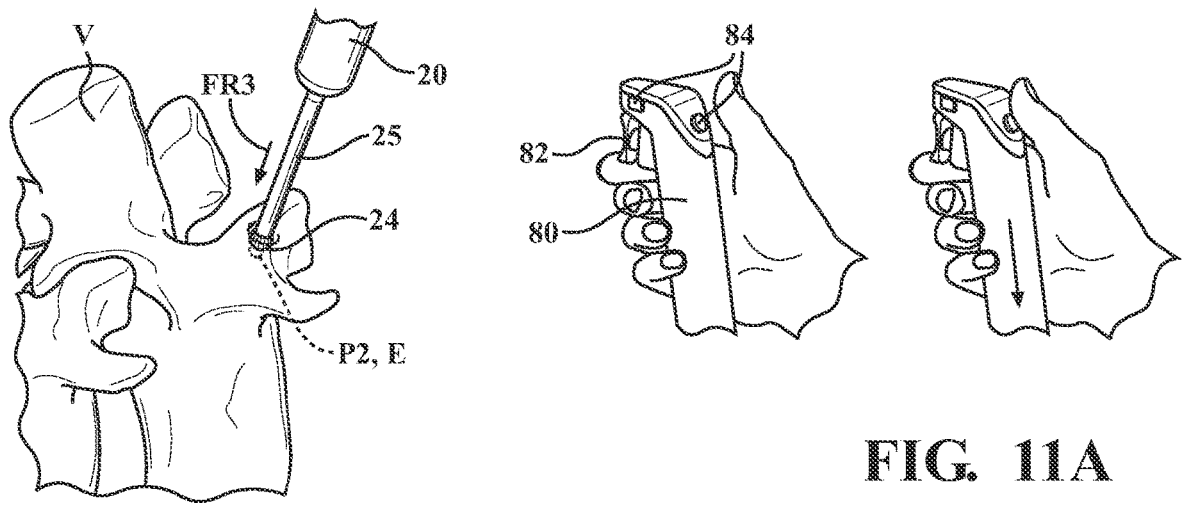
FIGS. 11A-11F illustrate progressive robotically controlled movement and feed rate control of the tool along the target axis for pedicle cannulation further utilizing the control interface coupled to the end effector.

In FIG. 11A, the tool 20 and/or bur 24 is now well-positioned for pedicle cannulation along the target axis (TA) at the second position P2. With the tool 20 and/or bur 24 stopped at the second position P2, the system may request the user to perform another confirmation process as a second check considering the imminent contact between the tool 20 and/or bur 24 and the vertebra (V). The confirmation process can be like any example described above, or variant thereof. Once confirmation is received, the user once again depresses the button 84, and the robotic manipulator 14 advances the tool 20 and/or bur 24 along target axis (TA) in the semi-autonomous mode according to a third feed rate, which may be slower than the first and second feed rates. For example, the third feed rate may be 1-3 mm per second. This third feed rate may be designated by the system in order to prevent user error.

Figure 11B:
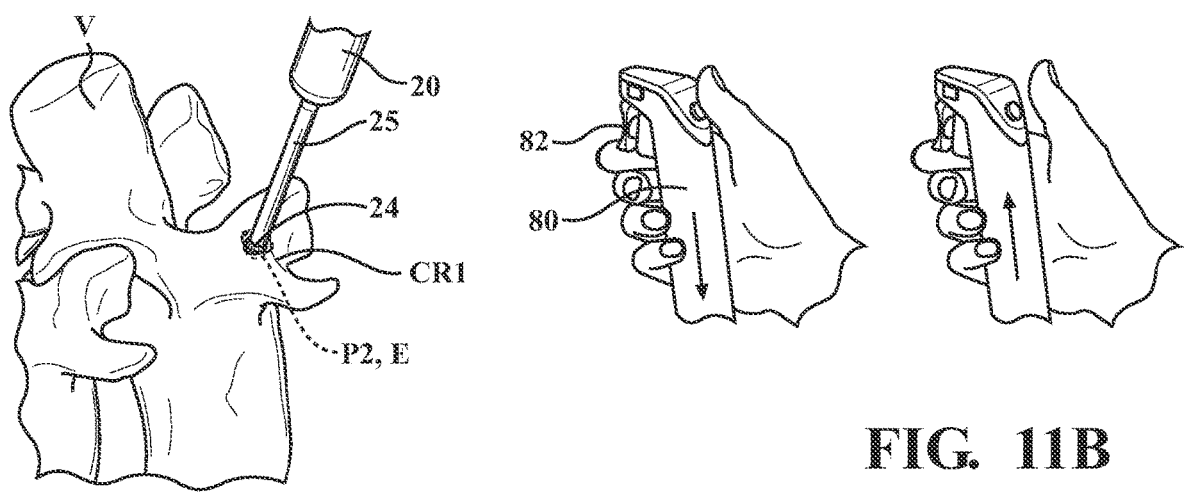

The slowness of this third feed rate is suitable because the tool 20 and/or bur 24 will engage the first cortical region (CR1) at this third feed rate, as shown in FIG. 11B. In FIG. 11B, user can depresses the trigger 82 to activate the bur 24 for milling while also pressing the button 84 to advance the tool 24 at the third feed rate to advance the bur 24 into contact with the first cortical region (CR1). The tool 20 and/or bur 24 begins to mill the first cortical region (CR1) along the target axis (TA) at the entry point (E).

For any examples described herein, the one or more controllers 30, 60, 62 can define a first length of the target axis (TA) and a second length of the target axis (TA) and assign different operational parameters for each length. For example, a length of the target axis (TA) can be defined between reference points, such as P1 and P2. Other points and lengths may be defined. These lengths can be defined in the navigation system 32 and can be associated with the surgical plan, virtual boundary, and/or virtual model of the vertebra (V). In one example, different designated feed rates can be set for one or more these lengths. In another example, as described below, controller managed feed rate control can be set for one or more lengths and user managed feed rate control can be set for one or more other lengths of the target axis (TA). The one or more controllers 30, 60, 62 can also enable semi-autonomous mode control for certain lengths of the target axis (TA) and enable manual mode control for other lengths of the target axis (TA). Additionally, the one or more controllers 30, 60, 62 can enable non-cutting mode control for certain lengths of the target axis (TA) and enable cutting-mode control for other lengths of the target axis (TA). In yet another example, the one or more controllers 30, 60, 62 can command a cutting speed (rpm) of the tool 20 and/or bur 24 for certain lengths of the target axis (TA) and enable user managed control of the cutting speed for other lengths of the target axis (TA). Any combination of these parameters is possible for any defined length of the target axis (TA). Furthermore, designated operational parameters can be defined by single values, or alternatively by a limit (upper or lower) or a range of designated values. For example, a designated feed rate can be defined between 25-30 mm per second, while enabling the user to have a hybrid form of control to manually manage the feed rate, but within the designated range. Additionally, any of the described techniques for controlling operating parameters can be dependent on whether the TCP of the tool 20 and/or bur 24 is off the target axis (TA) (virtual boundary) (as shown in FIG. 10A) or on the target axis (TA) (as shown in FIG. 10C).

With continued reference to FIG. 11B, the user may desire to reverse the tool 20 and/or bur 24 direction along the target axis (TA) to pull the tool 20 and/or bur 24 away from the entry point (E). For instance, such control may be desired to visually confirm the location of the entry point (E), otherwise inspect the milled entry point (E), and/or adjust tool 20 and/or bur 24 operation or trajectory to address milling conditions, such as potential skiving. To implement this reversal of direction, the user can release the button 84, which can signal the one or more controllers 30, 60, 62 to pull the tool 20 and/or bur 24 away from the vertebra (V) along the target axis (TA).

With any contact between the tool 20 and/or bur 24 and the vertebra (V), the one or more sensors 70 are configured to sense forces applied to the tool 20 and/or bur 24 by the vertebra (V) according to any manner as described in the previous sections. Measurements from the sensors 70 can provide input, among other things, for facilitating advanced feed rate control relative to the vertebra (V). Namely, the one or more controllers 30, 60, 62 can adjust the feed rate in response to the forces applied to the tool 20 and/or bur 24, as sensed by the sensors 70. For instance, the one or more controllers 30, 60, 62 can analyze measurements from the one or more sensors 70 to detect a transition between the first cortical region (CR1) and the cancellous bone region (CBR) or between the cancellous bone region (CBR) and the second cortical region (CR2) in the manner described above.

Figure 11C:
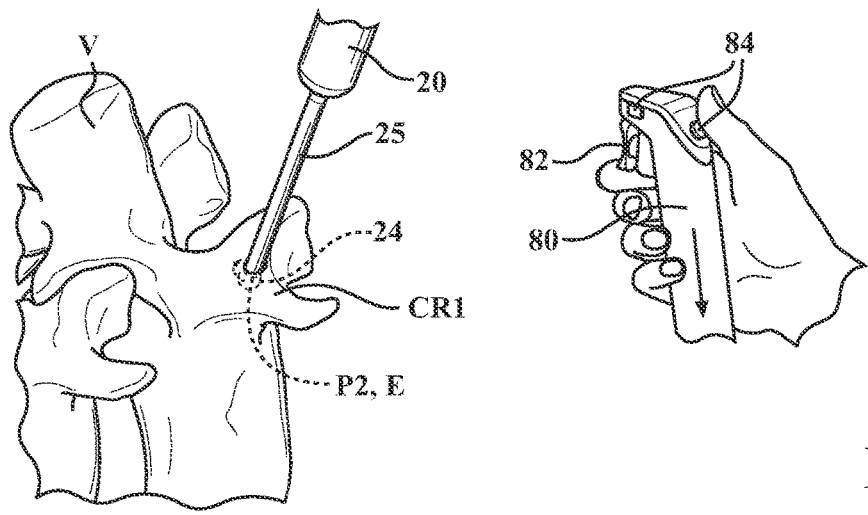

In FIG. 11C, the bur 24 has penetrated the first cortical region (CR1) and enters the cancellous bone region (CBR). This transition can be detected by signals from the sensors 70. In response to detecting the transition between the first cortical region (CR1) and the cancellous bone region (CBR), the one or more controllers 30, 60, 62 can control the robotic manipulator 14 to move the tool 20 and/or bur 24 along the target axis (TA) according to yet another feed rate, that is different from the feed rate utilized to mill the entry point (E) at the first cortical region (CR1).

Within the cancellous bone region (CBR), the one or more controllers 30, 60, 62 are configured to release designated feed rate control, thereby enabling the user to define/select and operate the tool 20 and/or bur 24 according to any feed rate desired by the user. In one example, the feed rate to penetrate the first cortical region (CR1) is less than (slower) the feed rate utilized to advance the tool 20 and/or bur 24 through the cancellous bone region (CBR). This may be done because skiving at the entry point (E) is no longer a potential issue when the TCP is within the cancellous bone region (CBR). In other words, skiving is not an issue within the cancellous bone region (CBR). Other practical reasons may exist for releasing feed rate control to the user within the cancellous bone region (CBR).

As described in previous sections, the depth of displacement of the TCP can relative to the first cortical region (CR1) can be detected by the sensors 70, the navigation system 32, or any other suitable method. In one example, the release of the designated feed rate control by the one or more controllers 30, 60, 62 can be triggered by a detected depth of the TCP, e.g., if the TCP is at a depth of 5 mm below the first cortical region (CR1). The depth can also be dependent on the geometry of the bur 24. Other depths are contemplated. As previously described, the one or more controllers 30, 60, 62 can also define designated feed rates for certain lengths of the target axis (TA) and to release designated feed rate control to the user for other lengths of the target axis (TA).

Figure 11D:
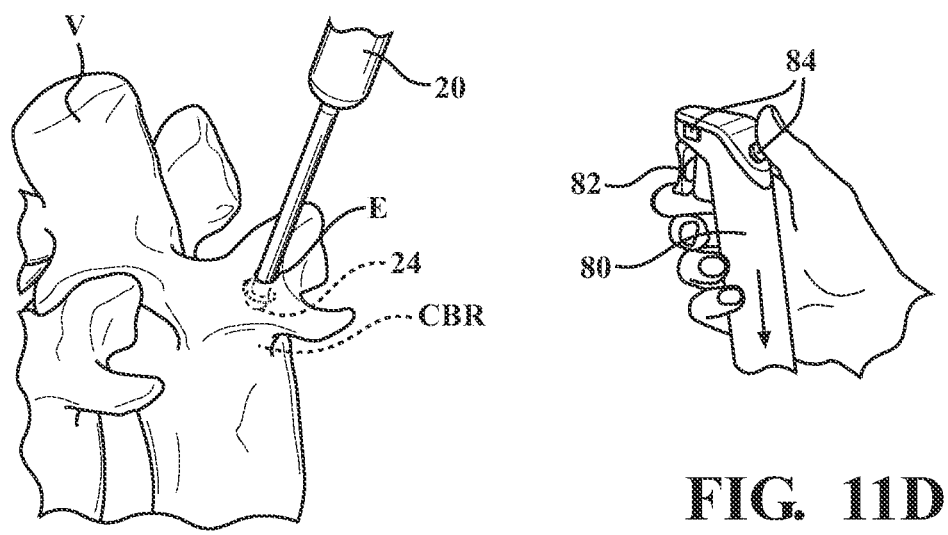

In FIG. 11D, the bur 24 continues to displace cancellous bone region (CBR) for pedicle bone cannulation. This can be done in either the cutting mode or non-cutting mode, as described above. The feed rate is managed by the operator and instead of being designated by the one or more controllers 30, 60, 62. The user depresses the button 84 to advance the tool 20 and/or bur 24 in the cancellous bone region (CBR) according to a feed rate that the user controls. Meanwhile, the rotational speed of the bur 24 can be defined by the one or more controllers 30, 60, 62 or manually adjusted by the operator. In one example, up to 250 rpm is allowed within the cancellous bone region (CBR). Rotational speed limitations or allowances can be activated by the one or more controllers 30, 60, 62 dependent on detected presence of the TCP being within the cancellous bone region (CBR).

Figure 11E:
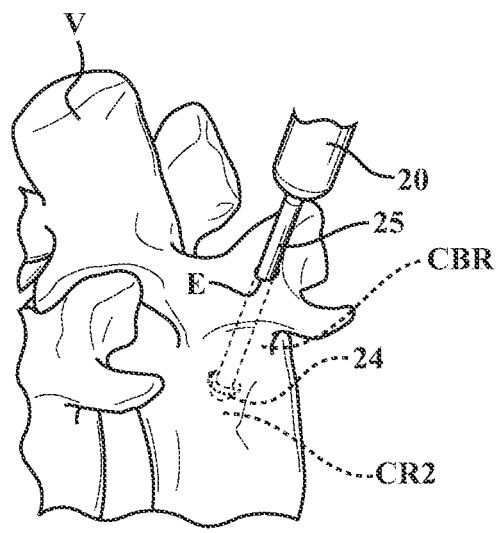

In FIG. 11E, the bur 24 continues to displace cancellous bone region (CBR) until it reaches the second cortical region (CR2). At this sensitive location, feedback from the sensors 70 can be utilized to control the tool 20 and/or bur 24 to reduce forces with the second cortical region (CR2) according to any manner described above.

Figure 11F:
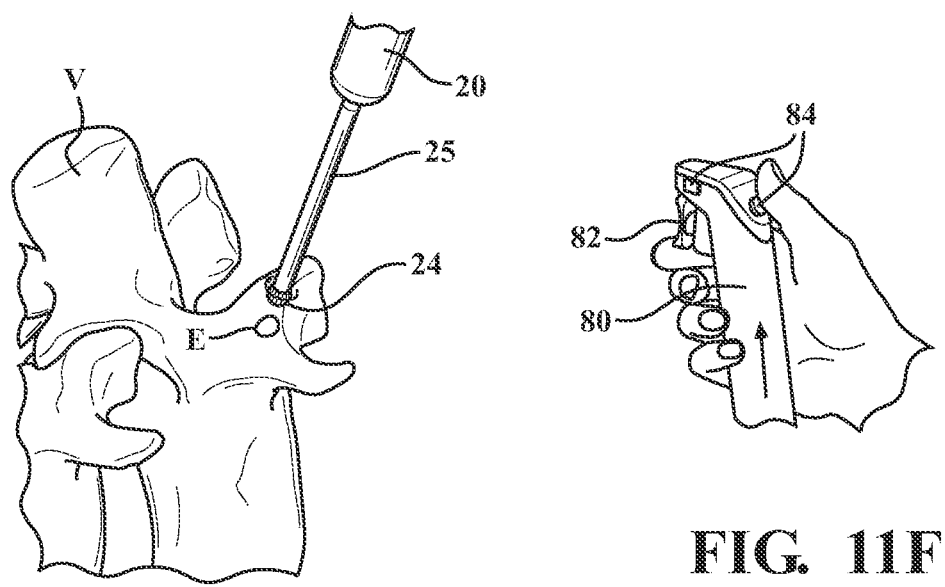

In FIG. 11F, the tool 20 and/or bur 24 is retracted away from the vertebra (V) along the target axis (TA). This retraction can be in response to feedback from the sensors 70. For example, once the second cortical wall (CR2) is detected, the one or more controllers 30, 60, 62 can automatically instruct the robotic manipulator 14 to pull the tool 20 and/or bur 24 in the opposite direction away from the second cortical region (CR2). This can be done based on the assumption that cannulation is complete once the second cortical wall (CR2) is reached. This automatic switching of direction can be performed while the user continues to hold the button 84 for feed rate advancement. The one or more controllers 30, 60, 62 can reverse the feed rate direction. The user can also manually engage the control interface 80 for switching the tool 20 and/or bur 24 direction along the target axis (TA). Any tactile button, sequence, or paradigm can be utilized to trigger the switch of tool 20 and/or bur 24 direction. Furthermore, the tool 20 and/or bur 24 can be retracted away from the vertebra (V) along the target axis (TA) in response to the one or more controllers 30, 60, 62 detecting a predetermined depth of the TCP relative to any suitable landmark of the vertebra (V). The predetermined depth can be defined relative to the virtual model and visualized to the user by the navigation system 32.

As the tool 20 and/or bur 24 remains in the cancellous bone region (CBR) but is exiting in the direction of the target axis (TA), the rotational speed limitations or allowances can remain activated by the one or more controllers 30, 60, 62. Once the tool 20 and/or bur 24 fully exits the vertebra (V), as shown in FIG. 11F, the detected presence of the TCP is no longer within the cancellous bone region (CBR) and the rotational speed limitations or allowances are deactivated. In one example, the operator can no longer operate the bur 24 up to 250 rpm once the tool 20 and/or bur 24 has exited the vertebra. The techniques and control interface 80 methods described with reference to FIGS. 10 and 11 can be utilized with any combination of control techniques or features described with reference to FIGS. 3-9.

Several examples have been discussed in the foregoing description. However, the examples discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system comprising:
   a surgical tool;
   a robotic manipulator comprising a plurality of links and joints and being configured to support and move the surgical tool for treating a bone structure;
   a navigation system configured to track the surgical tool and the bone structure; and
   one or more controllers coupled to the robotic manipulator and the navigation system, the one or more controllers being configured to:
   obtain a virtual model of the bone structure;
   define a first virtual boundary relative to the virtual model of the bone structure, wherein the first virtual boundary has a first constraint parameter;
   define a second virtual boundary relative to the virtual model of the bone structure, wherein the second virtual boundary has a second constraint parameter that is different than the first constraint parameter;
   register the virtual model and the first and second virtual boundaries to the bone structure; and
   control the robotic manipulator to:
   move the surgical tool relative to the bone structure and relative to the first and second virtual boundaries;
   constrain movement of the surgical tool relative to the first virtual boundary in accordance with the first constraint parameter; and
   constrain movement of the surgical tool relative to the second virtual boundary in accordance with the second constraint parameter.

2. The surgical system of claim 1, wherein the first virtual boundary is defined relative to a region external to the bone structure and the second virtual boundary is defined relative to an internal region of the bone structure.

3. The surgical system of claim 1, wherein the bone structure has a first region and a second region, and wherein the one or more controllers are configured to:
  detect a transition of the surgical tool from the first region to the second region; and
  in response to detection of the transition, activate one of the first virtual boundary and the second virtual boundary and adjust control of one or more of movement of the robotic manipulator and operation of the surgical tool.

4. The surgical system of claim 1, wherein the one or more controllers are configured to:
  obtain a location of a first feature and a second feature relative to the virtual model of the bone structure;
  receive an indication of a first sensitivity of the first feature;
  receive an indication of a second sensitivity of the second feature, the second sensitivity being different than the first sensitivity;
  define the first virtual boundary relative to the first feature;
  configure the first constraint parameter of the first virtual boundary based on the first sensitivity;
  define the second virtual boundary relative to second feature; and
  configure the second constraint parameter of the second virtual boundary based on the second sensitivity.

5. The surgical system of claim 1, wherein the first virtual boundary is virtually connected to the second virtual boundary.

6. The surgical system of claim 1, wherein
  the first virtual boundary is shaped to provide a first compliance for movement of the surgical tool relative to the first virtual boundary;
  the second virtual boundary is shaped to provide a second compliance for movement of the surgical tool relative to the second virtual boundary; and
  the first compliance enables either greater or lesser movement of the surgical tool than the second compliance.

7. The surgical system of claim 1, wherein:
  the first constraint parameter is a first stiffness parameter;
  the second constraint parameter is a second stiffness parameter; and
  the first stiffness parameter is either more stiff or less stiff than the second stiffness parameter.

8. The surgical system of claim 1, wherein the virtual model of the bone structure comprises a cortical wall and the one or more controllers are configured to define one or both of the first virtual boundary and the second virtual boundary relative to the cortical wall.

9. The surgical system of claim 1, wherein one of the first virtual boundary and the second virtual boundary is configured as a line haptic.

10. The surgical system of claim 1, wherein:
  the first virtual boundary is configured as a virtual mesh; and
  the one or more controllers are configured to control the robotic manipulator to constrain movement of the surgical tool relative to the virtual mesh using a reactive force generated in accordance with the first constraint parameter to repel the surgical tool away from the virtual mesh.

11. The surgical system of claim 1, wherein the bone structure comprises one or more actual anatomical landmarks, and the navigation system is configured to track an actual position of the surgical tool, and wherein:
  the one or more controllers are configured to control the robotic manipulator to cause the surgical tool to interact with one or more of the actual anatomical landmarks;
  one or more sensors are configured to sense actual forces applied to the surgical tool by one or more of the actual anatomical landmarks; and
  the one or more controllers are configured to:
    obtain the virtual model of the bone structure comprising one or more virtual anatomical landmarks;
    store data correlating expected force measurements from the one or more sensors and expected positions of the surgical tool to one or more of the virtual anatomical landmarks;
    receive actual force measurements from the one or more sensors based on actual forces applied to the surgical tool by one or more of the actual anatomical landmarks;
    receive the actual position of the surgical tool from the navigation system;
    compare the actual force measurements from the one or more sensors and the actual position of the surgical tool from the navigation system with the expected force measurements and the expected positions of the surgical tool to associate one or more of the actual anatomical landmarks with one or more of the virtual anatomical landmarks; and
    register the virtual model to the bone structure based on association of one or more of the actual anatomical landmarks with one or more of the virtual anatomical landmarks.

12. A method of operating a surgical system, the surgical system comprising a surgical tool, a robotic manipulator comprising a plurality of links and joints and being configured to support and move the surgical tool for treating a bone structure, a navigation system configured to track the surgical tool and the bone structure, and one or more controllers coupled to the robotic manipulator and the navigation system, the method comprising the one or more controllers performing the steps of:
  obtaining a virtual model of the bone structure;
  defining a first virtual boundary relative to the virtual model of the bone structure, wherein the first virtual boundary has a first constraint parameter;
  defining a second virtual boundary relative to the virtual model of the bone structure, wherein the second virtual boundary has a second constraint parameter that is different than the first constraint parameter;
  registering the virtual model and the first and second virtual boundaries to the bone structure; and
  controlling the robotic manipulator to move the surgical tool relative to the bone structure and relative to the first and second virtual boundaries;
  controlling the robotic manipulator to constrain movement of the surgical tool relative to the first virtual boundary in accordance with the first constraint parameter; and
  controlling the robotic manipulator to constrain movement of the surgical tool relative to the second virtual boundary in accordance with the second constraint parameter.

13. The method of claim 12, comprising the one or more controllers:
  defining the first virtual boundary relative to a region external to the bone structure; and defining the second virtual boundary relative to an internal region of the bone structure.

14. The method of claim 12, wherein the bone structure has a first region and a second region, and comprising the one or more controllers:
    detecting a transition of the surgical tool from the first region to the second region; and
    in response to detecting the transition, activating one of the first virtual boundary and the second virtual boundary and adjusting control of one or more of movement of the robotic manipulator and operation of the surgical tool.

15. The method of claim 12, comprising the one or more controllers:
    obtaining a location of a first feature and a second feature relative to the virtual model of the bone structure;
    receiving an indication of a first sensitivity of the first feature;
    receiving an indication of a second sensitivity of the second feature, the second sensitivity being different than the first sensitivity;
    defining the first virtual boundary relative to the first feature;
    configuring the first constraint parameter of the first virtual boundary based on the first sensitivity;
    defining the second virtual boundary relative to second feature; and
    configuring the second constraint parameter of the second virtual boundary based on the second sensitivity.

16. The method of claim 12, comprising the one or more controllers:
    defining the first virtual boundary to be shaped for providing a first compliance for movement of the surgical tool relative to the first virtual boundary;
    defining the second virtual boundary to be shaped for providing a second compliance for movement of the surgical tool relative to the second virtual boundary; and
    the first compliance enabling either greater or lesser movement of the surgical tool than the second compliance.

17. The method of claim 12, wherein the virtual model of the bone structure comprises a cortical wall, and comprising the one or more controllers:
    defining one or both of the first virtual boundary and the second virtual boundary relative to the cortical wall.

18. The method of claim 12, comprising the one or more controllers:
    defining the first virtual boundary as a virtual mesh; and
    controlling the robotic manipulator to constrain movement of the surgical tool relative to the virtual mesh using a reactive force generated in accordance with the first constraint parameter for repelling the surgical tool away from the virtual mesh.

19. The method of claim 12, wherein the bone structure comprises one or more actual anatomical landmarks, and the navigation system is configured to track an actual position of the surgical tool, and comprising the one or more controllers:
    controlling the robotic manipulator to cause the surgical tool to interact with one or more of the actual anatomical landmarks;
    obtaining, from one or more sensors, actual forces applied to the surgical tool by one or more of the actual anatomical landmarks;
    obtaining the virtual model of the bone structure comprising one or more virtual anatomical landmarks;
    storing data correlating expected force measurements from the one or more sensors and expected positions of the surgical tool to one or more of the virtual anatomical landmarks;
    receiving actual force measurements from the one or more sensors based on actual forces applied to the surgical tool by one or more of the actual anatomical landmarks;
    receiving the actual position of the surgical tool from the navigation system;
    comparing the actual force measurements from the one or more sensors and the actual position of the surgical tool from the navigation system with the expected force measurements and the expected positions of the surgical tool for associating one or more of the actual anatomical landmarks with one or more of the virtual anatomical landmarks; and
    registering the virtual model to the bone structure based on associating one or more of the actual anatomical landmarks with one or more of the virtual anatomical landmarks.

20. A surgical navigation system comprising:
    a localizer being configured to track a bone structure; and
    one or more controllers coupled to the localizer and being configured to:
        obtain a virtual model of the bone structure;
        define a first virtual boundary relative to the virtual model of the bone structure, wherein the first virtual boundary has a first constraint parameter;
        define a second virtual boundary relative to the virtual model of the bone structure, wherein the second virtual boundary has a second constraint parameter that is different than the first constraint parameter; and
        register the virtual model and the first and second virtual boundaries to the bone structure.

* * * * *